United States Patent
Meyer et al.

(10) Patent No.: US 12,408,911 B2
(45) Date of Patent: Sep. 9, 2025

(54) WIRELESS-ENABLED SURGICAL SUTURE NEEDLE

(71) Applicants: THE GENERAL HOSPITAL CORPORATION, Boston, MA (US); MASSACHUSETTS INSTITUTE OF TECHNOLOGY, Cambridge, MA (US)

(72) Inventors: Matthew J. Meyer, North Garden, VA (US); Rahul Bhattacharyya, Lowell, MA (US); Wilton Cahn Levine, Needham, MA (US); Sai Nithin R. Kantareddy, Cambridge, MA (US); Dustin R. Long, Seattle, WA (US); Sanjay E. Sarma, Lexington, MA (US); David H. Bartels, Williamstown, MA (US); Devan D. Bartels, Williamstown, MA (US); Matthew M. Vanneman, Cambridge, MA (US)

(73) Assignees: THE GENERAL HOSPITAL CORPORATION, Boston, MA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 773 days.

(21) Appl. No.: 17/055,624

(22) PCT Filed: May 14, 2019

(86) PCT No.: PCT/US2019/032103
§ 371 (c)(1),
(2) Date: Nov. 16, 2020

(87) PCT Pub. No.: WO2019/222139
PCT Pub. Date: Nov. 21, 2019

(65) Prior Publication Data
US 2021/0204936 A1 Jul. 8, 2021

Related U.S. Application Data

(60) Provisional application No. 62/671,084, filed on May 14, 2018.

(51) Int. Cl.
*A61B 90/90* (2016.01)
*A61B 17/06* (2006.01)
(Continued)

(52) U.S. Cl.
CPC .. *A61B 17/06066* (2013.01); *A61B 17/06166* (2013.01); *A61B 90/98* (2016.02); *A61B 2017/00221* (2013.01)

(58) Field of Classification Search
CPC ... A61B 90/90; A61B 90/98; A61B 17/06166; A61B 2017/00221; A61B 17/06066;
(Continued)

(56) References Cited

U.S. PATENT DOCUMENTS 3,035,583 A * 5/1962 Stoltz ............. A61L 17/145
606/228
3,722,440 A 3/1973 Garashi et al.
(Continued)

OTHER PUBLICATIONS

PCT International Search Report and Written Opinion for corresponding International Application Serial No. PCT/US19/32103, mailed Jul. 22, 2019, pp. 1-15.

*Primary Examiner* — Brooke Labranche
*Assistant Examiner* — Christina C Lauer
(74) *Attorney, Agent, or Firm* — Tarolli, Sundheim, Covell & Tummino LLP

(57) ABSTRACT

A suture needle apparatus includes a needle body and a radio-frequency identification ("RFID") chip disposed
(Continued)

proximate to the needle body. The RFID chip is encoded with an identifying information associated with the suture needle apparatus. The RFID chip includes an electromagnetic coupling element. A suture thread is operatively coupled to the needle body. At least one of the needle body and the suture thread is an antenna selectively electromagnetically coupled to the RFID chip and, when coupled, is configured to wirelessly communicate the identifying information responsive to radio-frequency interrogation of the suture needle apparatus. A method of providing a suture needle apparatus is also disclosed.

19 Claims, 12 Drawing Sheets

(51) Int. Cl.
*A61B 90/98* (2016.01)
*A61B 17/00* (2006.01)

(58) Field of Classification Search
CPC .... A61B 2017/06142; A61B 17/06004; A61B 2017/06052
See application file for complete search history.

(56) References Cited

U.S. PATENT DOCUMENTS

| | | | |
|---|---|---|---|
| 6,159,233 A * | 12/2000 | Matsuzawa | A61B 17/06066 606/223 |
| 7,439,863 B2 | 10/2008 | Suzuki et al. | |
| 7,501,947 B2 | 3/2009 | Youn | |
| 7,787,958 B2 | 8/2010 | Stevenson | |
| 2006/0186210 A1* | 8/2006 | Tethrake | G06K 19/005 235/492 |
| 2008/0042849 A1 | 2/2008 | Saito et al. | |
| 2008/0106419 A1 | 5/2008 | Sakama et al. | |
| 2014/0291409 A1 | 10/2014 | Nitta | |
| 2015/0265360 A1* | 9/2015 | Tatewaki | G06K 19/07758 606/174 |
| 2016/0058490 A1 | 3/2016 | Hotto et al. | |
| 2016/0148027 A1 | 5/2016 | Schoutens | |
| 2018/0050189 A1 | 2/2018 | Rump et al. | |

* cited by examiner

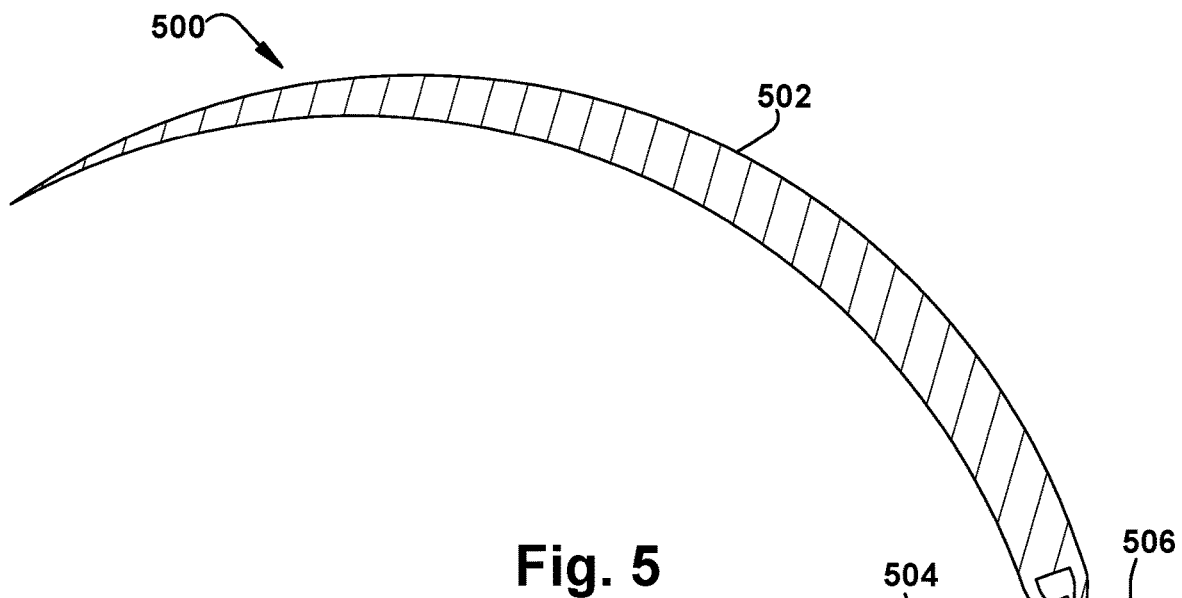
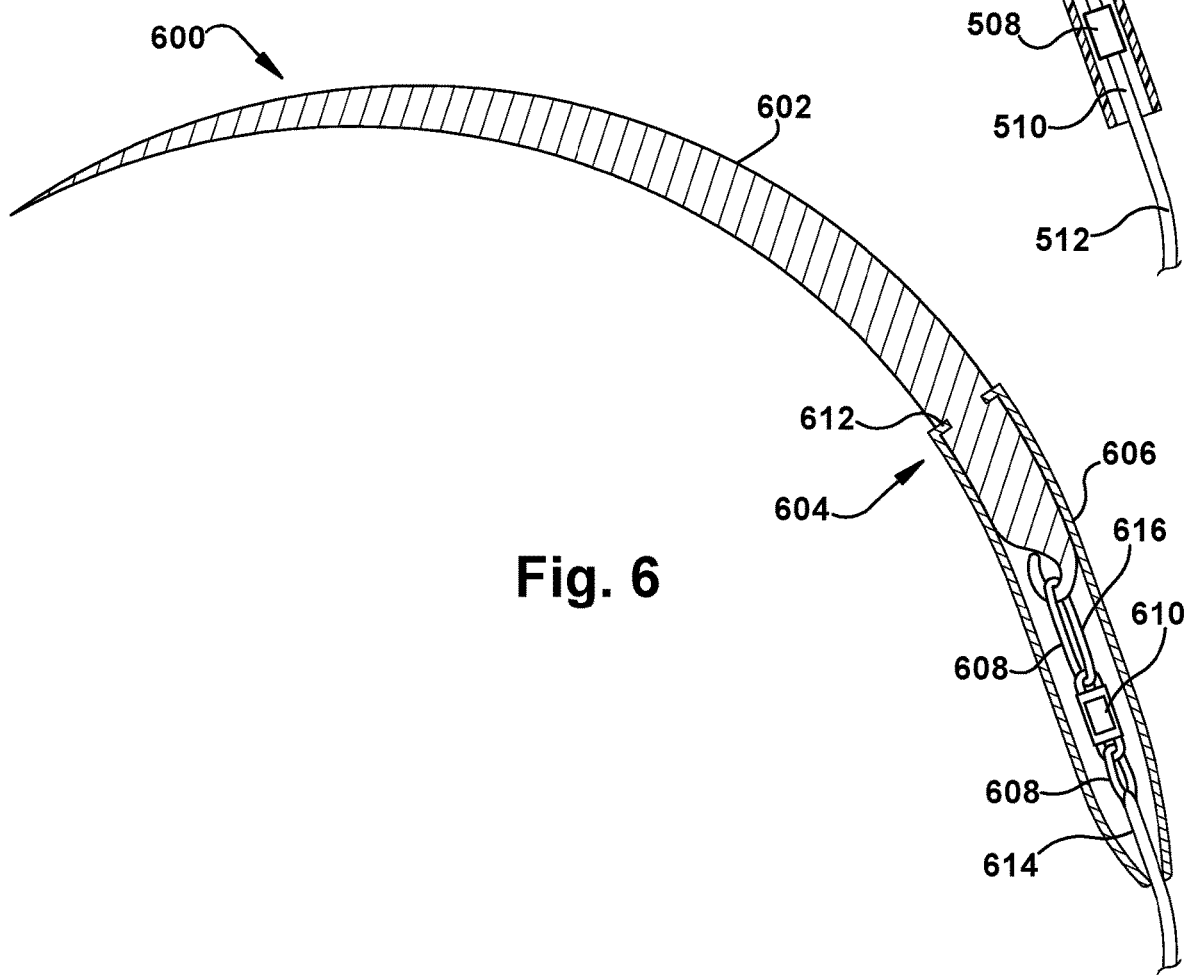

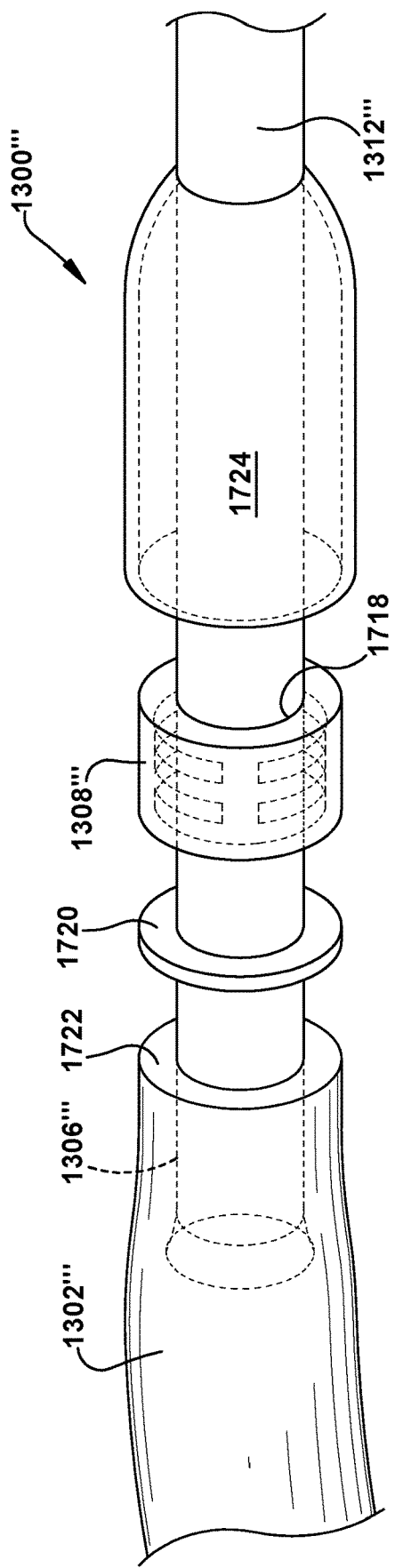
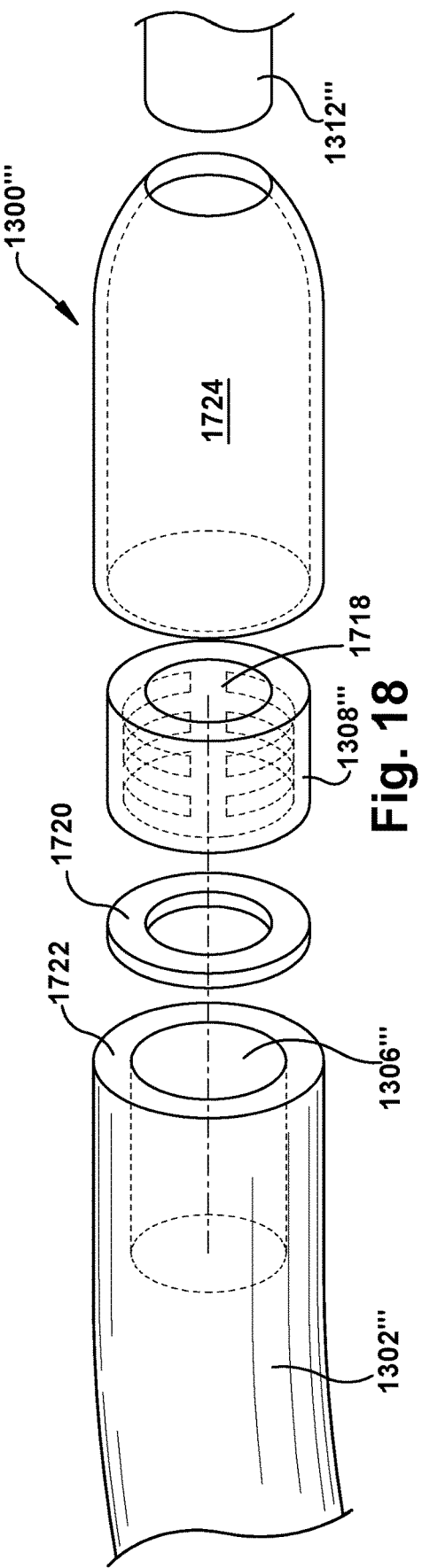

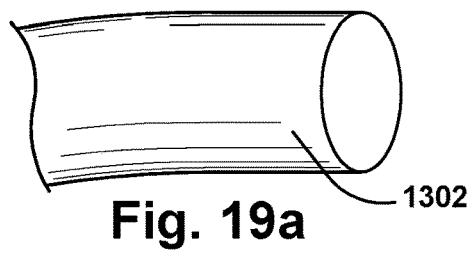
Fig. 19a  1302
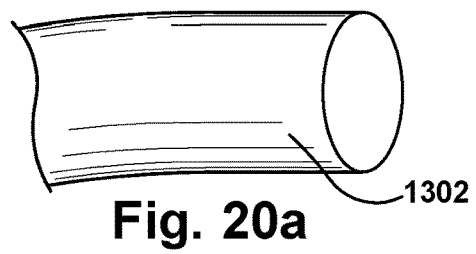
Fig. 20a  1302
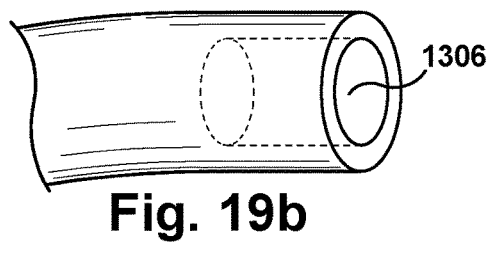
Fig. 19b  1306
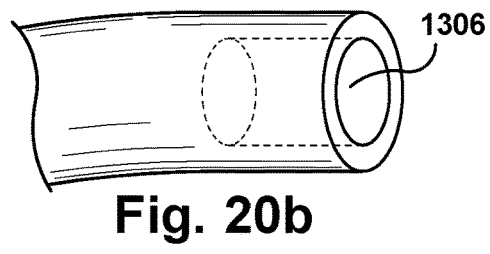
Fig. 20b  1306
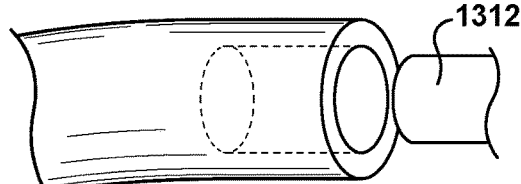
Fig. 19c  1312
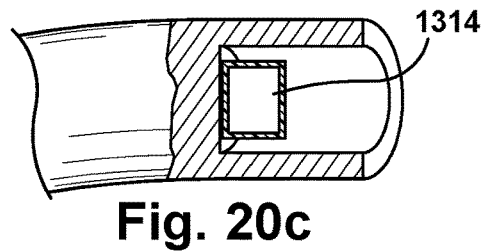
Fig. 20c  1314
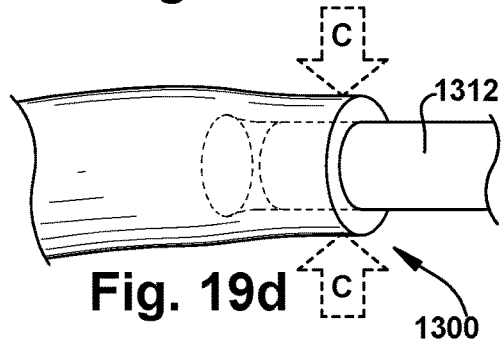
Fig. 19d  1300, 1312
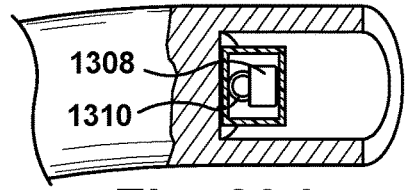
Fig. 20d  1308, 1310
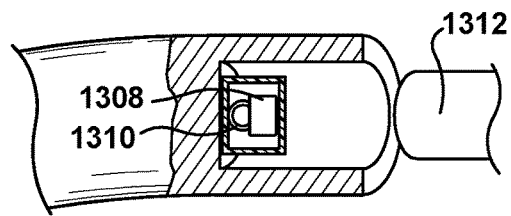
Fig. 20e  1308, 1310, 1312
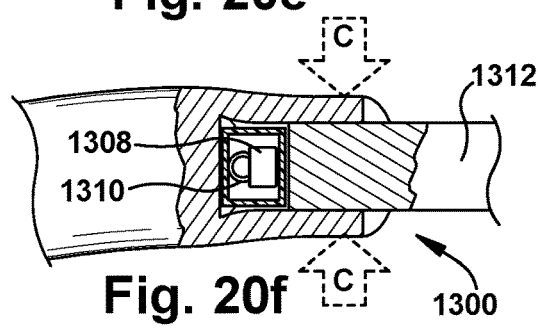
Fig. 20f  1308, 1310, 1312, 1300

WIRELESS-ENABLED SURGICAL SUTURE NEEDLE

RELATED APPLICATION

This application is a national phase application of and claims priority from PCT International Patent Application PCT/US2019/032103, filed May 14, 2019, which claims priority from U.S. Provisional Application No. 62/671,084, filed 14 May 2018. The subject matter of each of the aforementioned applications is incorporated herein by reference in its entirety.

TECHNICAL FIELD

This disclosure relates to an apparatus and method of manufacture of a surgical suture needle configured for wireless communication and, more particularly, to a wireless and/or RFID-enabled surgical suture needle.

BACKGROUND

Surgical suture needles are commonly used to hold separated body tissue together. The body tissue can be separated due to surgery or injury. During surgery, the number and location of all surgical devices (including surgical needles) within the surgical field should be regularly counted to ensure patient safety and to prevent retention of foreign objects within the patient. Protocols for maintaining accurate surgical counts remain predominantly manual processes and prone to human error.

Tracking systems based on high resolution video and wireless communication technologies have been proposed to improve the reliability and efficiency of this surgical count. Known tracking systems are capable of counting and locating larger objects, such as absorptive lap pads and hand-held surgical instruments, but are not capable of counting and locating smaller objects such as suture needles. The primary barriers to applying wireless tracking technologies to suture needles is their small size and traditional composition of metal which may interfere with signal transmission. However, missing or miscounted suture needles are the most common reason for an incorrect surgical count. Unlike larger instruments, needles can be difficult or impossible to visualize with x-rays that are performed to "rule out" the presence of a retained object. Thus, the prevalence of unresolved surgical counts involving a missing surgical needle remains high.

SUMMARY

In an aspect, a suture needle apparatus is described. The suture needle apparatus includes a needle body and a radio-frequency identification ("RFID") chip disposed proximate to the needle body. The RFID chip is encoded with an identifying information associated with the suture needle apparatus. The RFID chip includes an electromagnetic coupling element. A suture thread is operatively coupled to the needle body. At least one of the needle body and the suture thread is an antenna selectively electromagnetically coupled to the RFID chip and, when coupled, is configured to wirelessly communicate the identifying information responsive to radio-frequency interrogation of the suture needle apparatus.

In an aspect, a method of providing a suture needle apparatus is described. A needle body and a radio-frequency identification ("RFID") chip including an electromagnetic coupling element are provided. The RFID chip is encoded with information associated with the suture needle apparatus. The RFID chip is disposed proximate to the needle body. A suture thread is operatively coupled to the needle body. At least one of the needle body and the suture thread is selectively electromagnetically coupled to the RFID chip as an antenna. When the antenna and the RFID chip are electromagnetically coupled, the identifying information is wirelessly communicated responsive to radio-frequency interrogation of the suture needle apparatus.

BRIEF DESCRIPTION OF THE DRAWINGS

For a better understanding, reference may be made to the accompanying drawings, in which:

FIG. 5 is a schematic cross-sectional view of an example RFID-enabled surgical suture needle according to a fifth aspect;

FIG. 6 is a schematic cross-sectional view of an example RFID-enabled surgical suture needle according to a sixth aspect;

FIG. 17 is a schematic cross-sectional view of a portion of an example RFID-enabled surgical suture needle according to a fourteenth aspect.

FIG. 18 is an exploded view of the RFID-enabled surgical suture needle of FIG. 17.

FIGS. 19*a-d* schematically depict an example assembly sequence of a prior art surgical suture needle.

FIGS. 20*a-f* schematically depict an example assembly sequence of the RFID-enabled surgical suture needle of FIG. 13.

DETAILED DESCRIPTION

Figure 1:
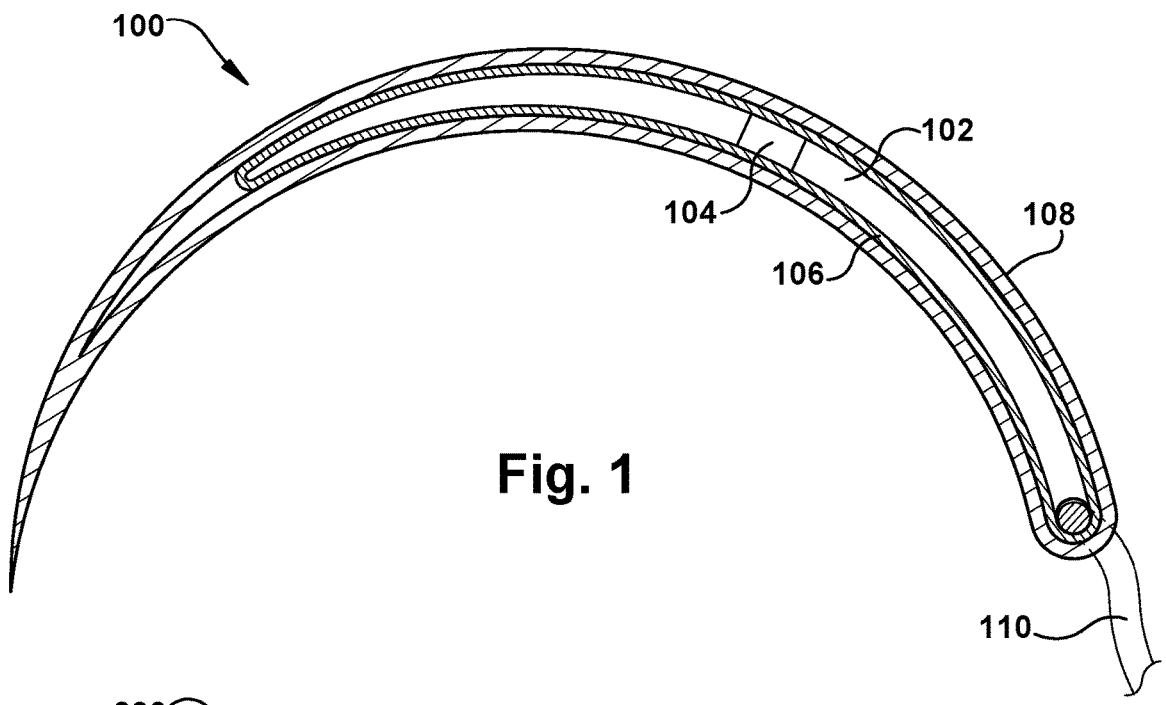
FIG. 1 is a schematic cross-sectional view of an example RFID-enabled surgical suture needle according to a first aspect.

The invention comprises, consists of, or consists essentially of the following features, in any combination.

Example surgical suture needles are described herein that address the barriers described and enable surgical suture needles to be equipped with wireless communication devices, which are described herein as radio-frequency identification ("RFID") wireless chips that house identifying information and antennas that permit wireless communication, thereby enabling labeling, counting, and location and time tracking of surgical suture needles. Although references herein are made specifically to surgical suture needles, the example designs may similarly be applied to other surgical tools such as scalpel blade, cautery blade, forceps, clamps, retractors, angiocatheter, catheter, hypodermic needle, biopsy needle, port, probe, sponge, cannula, balloon, capsule, wire, stimulator, sensor, stent, coil, bead, particle, plug, clip, staples, marker or any other desired surgical or interventional instrument or tool.

Although the examples described herein make specific reference to RFID technology, the example aspects may similarly be implemented using other suitable wireless communication technology such as, but not limited to, UHF, HF, NFC, and/or any suitable battery-less technology(ies) spanning across broad radio frequency spectrums.

As part of a system for enabling the surgical sharp count, the examples described herein can be used to inventory, count, track, and/or locate suture needles inside and outside of the operative field. Furthermore, the example aspects can facilitate augmented reality for minimally invasive surgical approaches as well as fully automated robotic surgeries by permitting the identification and localization of the suture needle. In addition, the example aspects shown and described herein could be used to assist with identification and/or localization of one or more items which are intended to remain within the patient's body over a longer period of time than the surgical procedure in which they are implanted.

A surgical suture needle for enabling labeling, counting, and/or location and time tracking includes a needle body and an RFID chip positioned proximate to the needle body. The RFID chip is encoded with identifying information associated with the suture needle, such as suture size, type, lot, unique identifier, expiration date, and other manufacturing information. The surgical suture needle includes an antenna for wirelessly communicating the identifying information. As will be described, the antenna may assume various forms, depending on the positioning of the RFID chip with respect to the needle body. Certain aspects of the surgical needle may also include a sheath made of RF lucent material that at least partially encloses and protects the RFID chip and the antenna. Because one limiting factor for RFID communication efficiency and range is an effective size of the antenna, it may be desirable, in some use environments, to have the antenna be a rather large structure of the entire surgical needle system.

A "sheath," as used herein is an outer covering for protecting the RFID chip from abrasion and damage which may result during use of the suture needle, during a sewing operation for example. The sheath is configured such that it will not interfere with the function of the suture needle. The sheath is also configured such that it allows RF energy to pass for the purpose of wireless communication.

An "inner core" as used herein is an RF lucent structure conforming to a shape of a suture needle.

Although the example suture needles described herein reference a single RFID chip, it should be appreciated that an example suture needle may benefit from including multiple RFID chips. For example, by including multiple RFID chips, a location of an example suture needle may be more easily identified using triangulation.

FIG. 1 illustrates a first aspect of an example RFID-enabled surgical suture needle ("suture needle") 100. The suture needle 100 includes an inner core 102 or needle body that maintains the form of the suture needle 100. The suture needle 100 further includes an RFID chip 104 embedded in the inner core 102. The RFID chip 104 is encoded with a unique identifier associated with a particular suture needle 100. The suture needle 100 further includes an antenna 106 that is linked to the RFID chip 104. The RFID chip 104 is also configured to wirelessly receive and transmit identifying information. The antenna 106 is located within an outer sheath 108. The antenna spans the surface of the inner core 102 in an orientation which may be modified to optimize various radiofrequency properties. In other words, the RFID chip 104 and antenna 106 are coextensive with the outer sheath 108. The antenna 106 may optionally be electrically isolated from the inner core 102 with an insulating film.

The outer sheath 108 at least partially encloses the antenna 106 and the RFID chip 104 and protects the antenna 106 and the RFID chip 104 from external trauma and from other trauma, for example, related to pressure from a needle driver. It should be appreciated that, in one example, the inner core 102 in combination with the embedded RFID chip 104 and the enveloping antenna 106, enclosed by the outer sheath 108, provides for a form factor similar to a form factor of a known suture needle and is therefore familiar to a surgeon. It should be further appreciated that, in other examples, the inner core 102 in combination with the embedded RFID chip 104 and the enveloping antenna 106, enclosed by the outer sheath 108, may provide for a different form factor.

A suture 110 extends from the end of the suture needle 100. It should be appreciated that suture needle 100 (as well as the other example suture needles described herein) may include an eye loop (not shown) for selectively receiving the suture 110 there through, or could instead be swaged—that is, manufactured with the suture 110 attached to the needle—as desired for a particular use environment.

The suture needle 100 may be at least partially constructed of radiofrequency ("RF") lucent material in order to allow radio waves to pass through without being blocked and without experiencing a loss in signal quality. In one example, both the inner core 102 and the outer sheath 108 may be constructed of the RF lucent material. In one example, the inner core 102 may be constructed of a traditional steel or alloy while the outer sheath 108 is constructed of RF lucent material. In such an example, an insulating film (not shown) may separate the inner core 102 from the RFID chip 104 and the antenna 106. Although certain types of a material may be RF lucent with respect to certain frequencies, the same material may be RF-opaque and block other radio frequencies from passing. Thus, the selection of the RF lucent material may vary by application.

In one example, the RF lucent material may include, for example, Kevlar® aramid fiber (available from DuPont Protection Technologies of Richmond, VA), a carbon fiber reinforced polymer ("CFRP"), and/or any other desired polymer. In one example, CFRP may be electrically conductive, a property which may be advantageously used in the present aspects. In one example, the RF lucent material may include an organic material such as bamboo. In one example, the RF lucent material may include obsidian. It should be appreciated that the above-listed materials are described for illustrative purposes and that any other suitable material that allows for radio frequencies to pass without significantly impacting the quality of the signal may be used as a RF lucent material in the example aspects. It should be further appreciated that the materials described might not yet be used in FDA-approved devices and may require FDA testing/approval before being utilized in the example aspects. Although the example RF lucent materials have been described with reference to the suture needle 100 illustrated in FIG. 1, the example RF lucent materials may similarly be used in constructing one or more of the additional example suture needles described below.

In one example, the suture 110 may be made of conductive fiber or other material or may be coated in a conductive material. In such an example, the suture 110 is electrically isolated from the outer sheath 108 but is electrically connected to the antenna 106 embedded in the inner core 102, thus forming a second arm or an extension of the antenna 106. In one example, the suture 110 electrically connected to the antenna 106 extends the overall length of the antenna 106. It should be appreciated that this increased antenna 106 length increases the amount of power available for RF communications. In one example, when extended read range is desired, a non-conductive RF lucent coating is used to bond, protect, or enhance, the electromagnetic properties of the suture needle 100.

Figure 2:
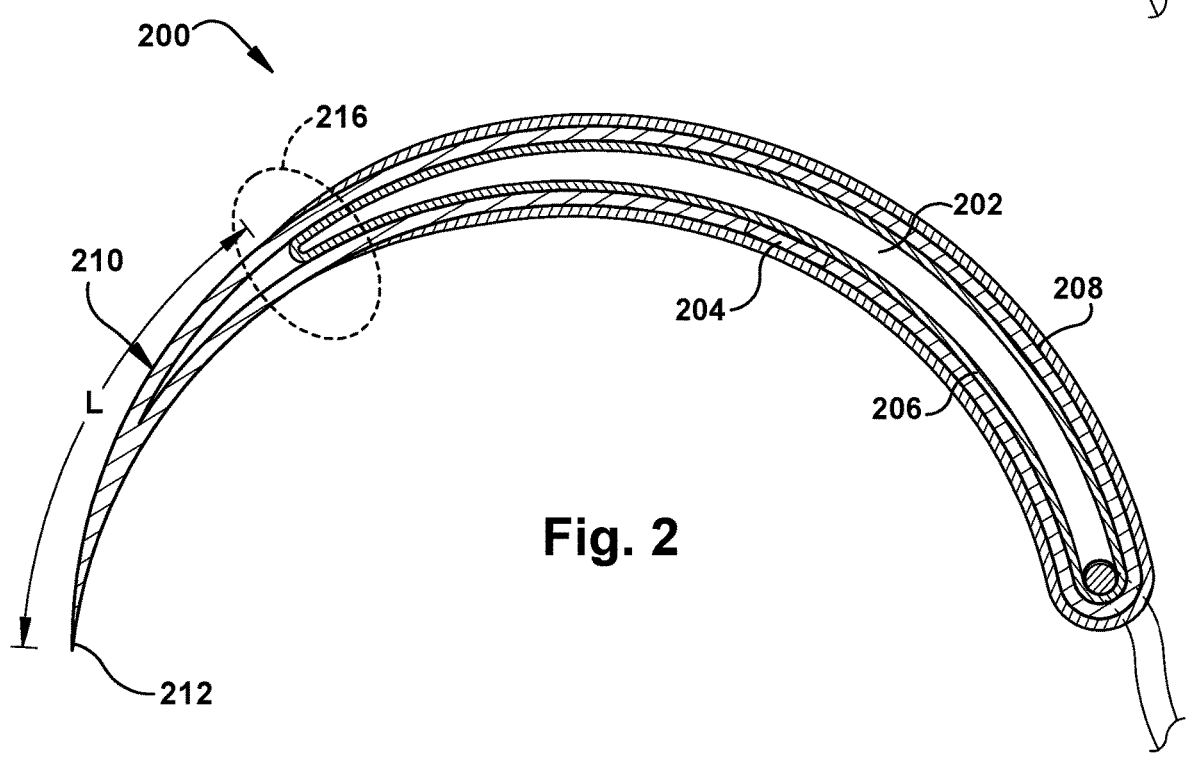
FIG. 2 is a schematic cross-sectional view of an example RFID-enabled surgical suture needle according to a second aspect.

FIG. 2 illustrates a second aspect of an RFID-enabled surgical suture needle ("suture needle") 200. The suture needle 200 of the second aspect, shown in FIG. 2, includes an RFID chip 204 and an antenna 206 embedded in or proximate to an inner core 202, and enveloped by an outer sheath 208. This comprises the body 214 of the suture needle 200. The inner core 202 and outer sheath 208 of the body 214, as previously described, is constructed of RF lucent material. In this example aspect, however, the suture needle 200 is formed of a hybrid construct. In particular, the suture needle 200 includes a load bearing tip 210 constructed of stainless steel (or other suitable material, such as, but not limited to, a steel alloy). The tip 210, which includes a point 212, extends along the body of the suture needle 200 for a length "L". The tip 210 is fused to the body 214 of the suture needle 200 at a bonding point 216. Bonding of the tip 210 to the body 214 may performed using any suitable techniques such as friction bonding, for example. It should be appreciated that the hybrid design of the suture needle 200 will provide a similar suturing experience and tactile feedback as compared to a known suture needle 100 while incorporating RFID technology.

Figure 3:
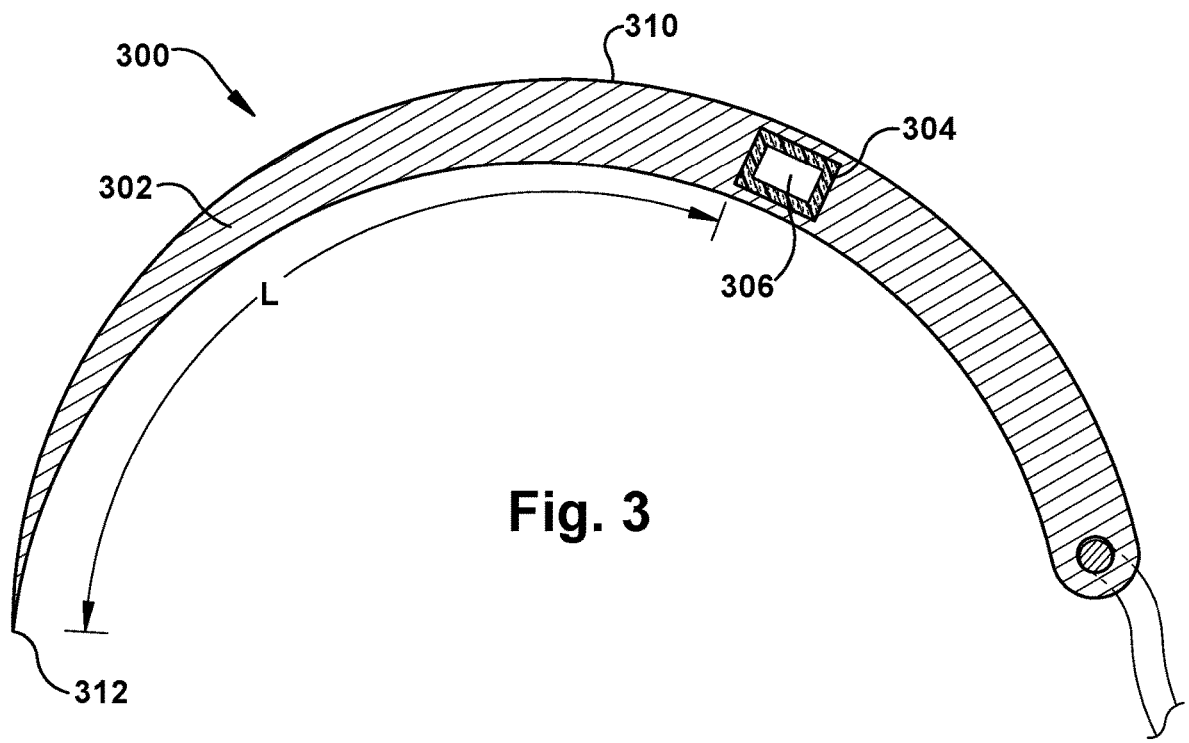
FIG. 3 is a schematic cross-sectional view of an example RFID-enabled surgical suture needle according to a third aspect.

FIG. 3 illustrates a third aspect of an example suture needle 300. A body 302 of the suture needle 300 may be constructed primarily of stainless steel (or other suitable conductive material, such as, but not limited to, a steel alloy). The suture needle 300 includes a relatively small gap or recess 304 cut into the body 302. The suture needle 300 further includes an RFID chip 306 spanning the recess 304. The recess 304 may be a square shape as illustrated or may be any other suitable shape for housing the RFID chip 306. The conductive needle body 302 is connected directly to the RFID chip 306 at the recess 304 and therefore functions as an antenna, thereby eliminating the need for additional hardware or components. The recess 304 contains an RF lucent non-conductive material that serves the dual purpose of A) structurally supporting the chip B) electrically isolating it from the metal underneath. In one example, the recess 304 as well as the RFID chip 306 are together coated with RF lucent material to prevent damage to the chip due to abrasive forces. It should be appreciated that the location of the recess 304 in the body 302 of the suture needle 300 will be at some length "L" from the point 312 which may be selected such that mechanical stress and pressure on the RFID chip 306 resulting from the suture needle 300 driver and tissue manipulation is minimized. In one example, the RFID chip 306 is potted into the recess 304 with epoxy. This protects the RFID chip 306, helps reduce friction, fosters mechanical integrity and support, and provides for a traditional needle form and shape.

In one example, the suture needle 300 further includes an outer sheath 310 that further protects the RFID chip 306 from external trauma and from other trauma related to pressure from needle driver.

It should be appreciated that, in the example suture needle 300, the RFID chip 306 is slim enough such that it can be disposed inside the recess 304. In one example, the RFID chip 306 is exposed and does not require a covering. In one example, the RFID chip 306 may be engraved onto the surface of the suture needle 300.

Figure 4:
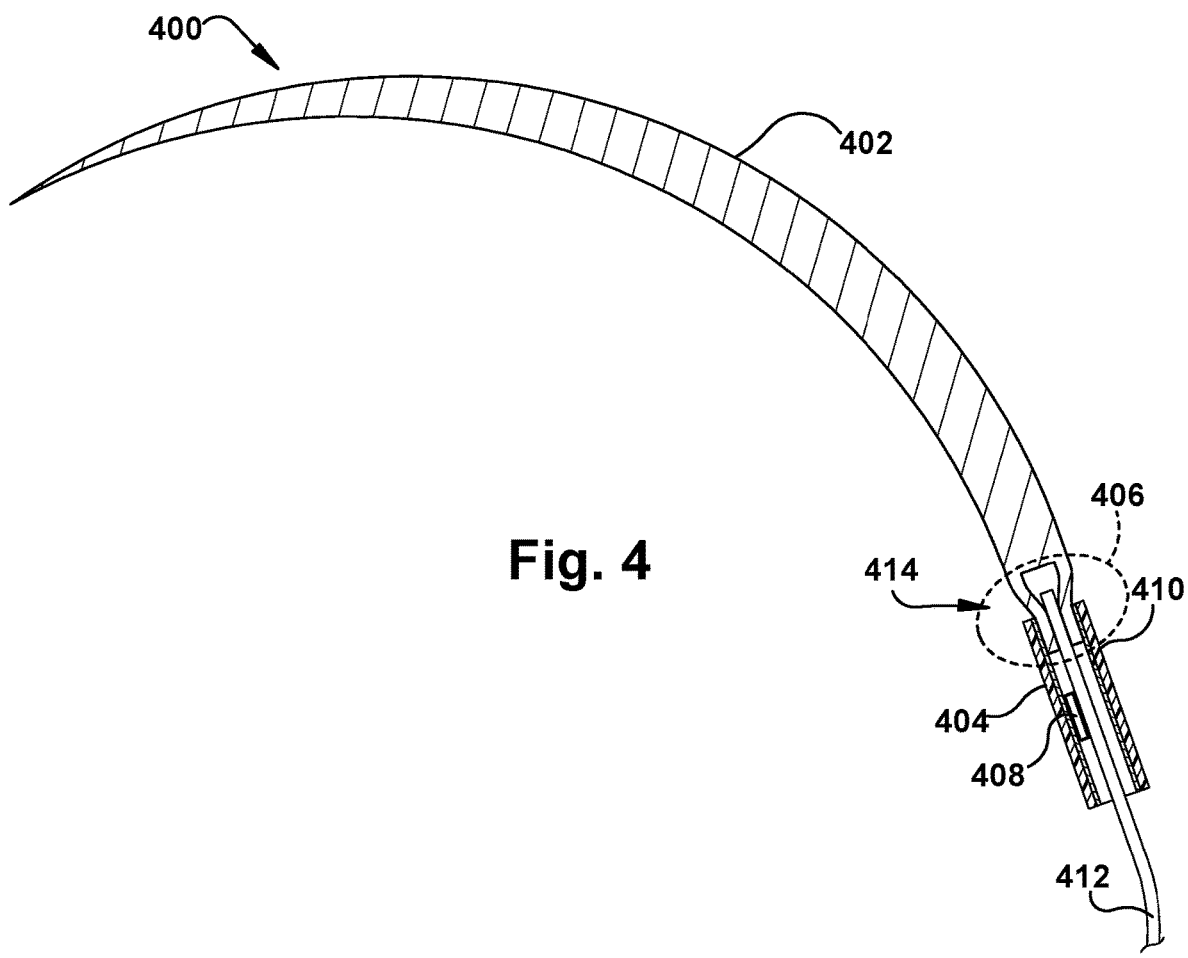
FIG. 4 is a schematic cross-sectional view of an example RFID-enabled surgical suture needle according to a fourth aspect.

FIG. 4 illustrates a fourth aspect of an example RFID-enabled surgical suture needle ("Suture needle") 400. The body 402 of the suture needle 400 is constructed primarily of stainless steel (or other suitable conductive material, such as, but not limited to, a steel alloy). The suture needle 400 includes a sheath 404 bonded to the suture needle 400 at bonding zone 406 at the swage end 414. In other words, the sheath 404 acts as a cap that goes on the swage end 414 of the suture needle 400. The sheath 404 includes an RFID chip 408 encoded with a unique identifier associated with the suture needle 400. An antenna is comprised of the metal needle body 402 and a length of conductive material 410 within the sheath which extends away from the bonding zone 406. The sheath extends from the needle body so as to maintain the silhouette of the suture needle 400 and to provide the surgeon with the familiar feel of a traditional suture needle. The sheath 404 is configured to allow for a suture 412 to extend out from the swage end, through the bonding zone 406, and out through the sheath 404. In one example, the sheath 404 may be at least partially constructed of RF lucent material as described.

FIG. 5 illustrates a fifth aspect of an example RFID-enabled surgical suture needle ("suture needle") 500. The suture needle 500 includes a body 502 constructed primarily of stainless steel (or other suitable material, such as, but not limited to, a steel alloy). At the swage end 504, the suture needle 500 includes a sheath 506 or a cap with an embedded RFID chip 508 encoded with a unique identifier associated with the suture needle 500. The metallic body 502 of the suture needle 500 serves as an antenna for wireless communication. In contrast to the example suture needle 400 illustrated in FIG. 4, however, portions of the metallic body 502 of the suture needle 500 do not extend and overlap the sheath 506. Rather, the suture needle 500 includes a conductive suture 510 that extends from the swage and through the sheath 506. The conductive suture 510 is at least partially made of a conductive material, thereby serving as an extension of the metallic body 502 as well as a trailing antenna. In one example, a non-conductive thread 512 extends out beyond the sheath 506 and thus resembles a traditional suture of a traditional suture needle 100. Thus, a portion of conductive suture 510 within the sheath 506 serves as a second arm of the antenna 510. In one example, to further facilitate wireless communication, at least a portion of the sheath 506 contains or is coated with an electrically conductive material.

FIG. 6 illustrates a sixth aspect of an example RFID-enabled surgical suture needle ("suture needle") 600. The suture needle 600 includes a body 602 constructed primarily of stainless steel (or other suitable material, such as, but not limited to, a steel alloy). At or near the swage end 604, the suture needle 600 includes a sheath 606 constructed of RF lucent material.

In one example, the sheath 606 may be coupled to the metallic body 602 at the swage end 604 using a clamp 612. It should be appreciated that other suitable bonding techniques may be used to couple the sheath 606 to the metallic body 602. Within the sheath 606, the suture needle 600 includes a conductive suture 608 coupled to the metallic body 602 at the swage end 604. The suture needle 600 further includes an RFID chip 610 encoded with a unique identifier associated with the suture needle 600. The RFID chip 610 is positioned such that it spans the metallic body 602 and the conductive suture 608, which form two arms of an antenna. It should be appreciated that, although the conductive suture 608 is in close proximity to the metallic body 602, the lagging end 614 of the conductive suture 608 remains electrically isolated from the metallic body 602 while the shorter end 616 of the conductive suture 608 is electrically connected to the metallic body 602.

Figure 7:
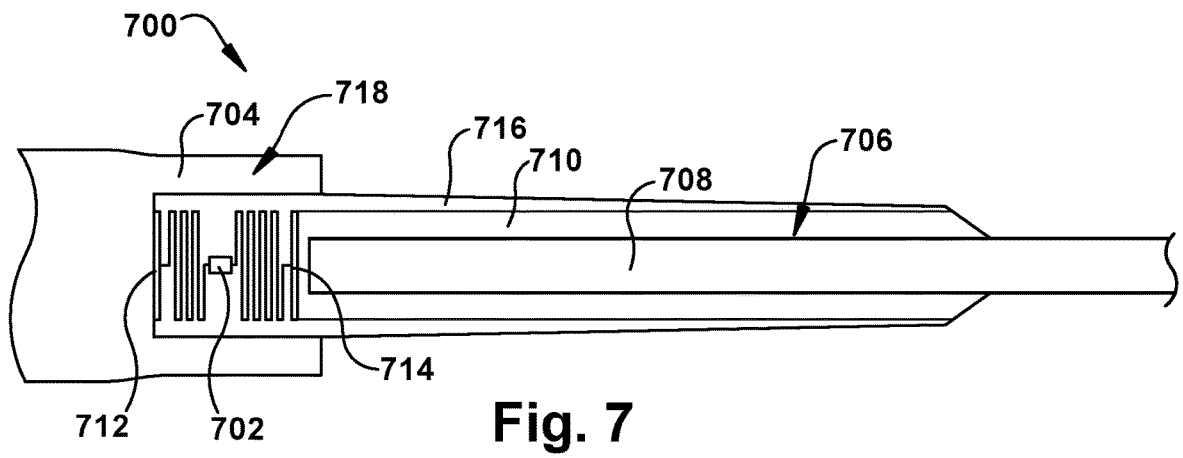
FIG. 7 is a schematic cross-sectional view of a portion of an example RFID-enabled surgical suture needle according to a seventh aspect.

The RFID chip 610 may be oriented in a variety of ways to facilitate contact as described. For example, as illustrated in a seventh aspect of an example RFID-enabled surgical suture needle ("suture needle") 700 in FIG. 7, the suture needle 700 includes an RFID chip 702 positioned axially between a metallic body 704 and a conductive suture 706. The conductive suture 706 includes a standard suture 708 covered by a conductive coating 710. A chip-body contact 712, shown here as a first end plate, connects the metallic body 704 to the RFID chip 702. Thus, the metallic body 704 and the conductive suture 706 together form the two arms of an antenna. A chip-suture contact 714, shown here as a second end plate, connects the conductive suture 706 to the RFID chip 702. The suture needle 700 includes an RF lucent sheath 716 constructed of RF lucent material that wraps around the conductive suture 706 and the RFID chip 702 and serves as an electrical insulator. In one example, a portion of the metallic body 704 may extend and partially overlap at least a portion the RFID chip 702 and the RF lucent sheath 716 at the swage end 718. The conductive suture 706, however, is not completely overlapped by the metallic body 704 as shown in the Figures.

Figure 8:
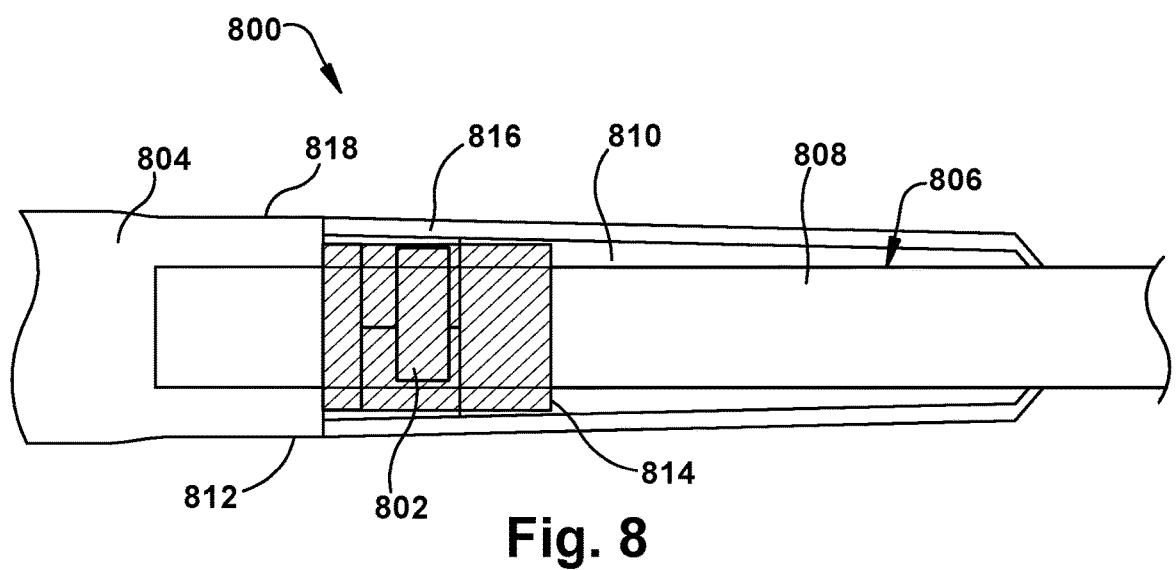
FIG. 8 is a schematic cross-sectional view of a portion of an example RFID-enabled surgical suture needle according to an eighth aspect.

In an eighth aspect of an example RFID-enabled surgical suture needle ("suture needle") 800, as illustrated in FIG. 8, the suture needle 800 includes an RFID chip 802 positioned between the metallic needle body 804 and a conductive suture 806. In this aspect, the RFID chip 802 is a donut-like disk, threaded onto string. The conductive suture 806 is formed from a standard suture 808 with conductive coating 810. A chip-body contact 812, shown as a first end plate, connects the metallic body 804 to the RFID chip 802. A chip-thread contact 814, shown as a second end plate, connects the conductive suture 806 to the RFID chip 802. Thus, the RFID chip 802 is a two-port connection such that the metallic needle body 804 serves as one arm of an antenna across a first port and the conductive suture 806 serves as a second arm of the antenna across a second port. The suture needle 800 includes an RF lucent sheath 816 constructed of RF lucent material that wraps around the conductive suture 806 and the RFID chip 802 and serves as an electrical insulator. The RF lucent sheath 816 is joined to the metallic body 804 at a swage end 818. In one example, a portion of the metallic body 804 may extend and partially overlap at least a portion of the conductive suture 806 at the swage end 818. The conductive suture 806 is not completely overlapped by the metallic body 804 as shown in the Figures.

Figure 9:
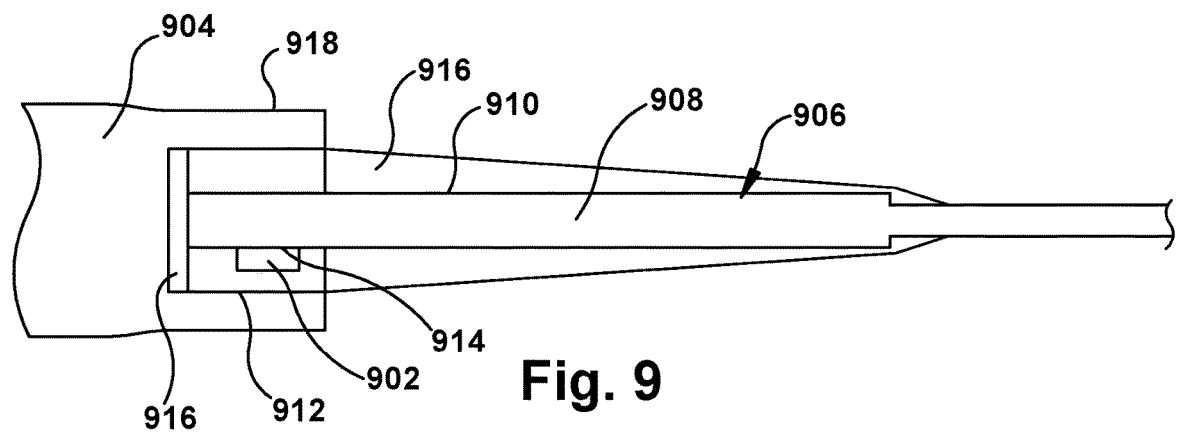
FIG. 9 is a schematic cross-sectional view of a portion of an example RFID-enabled surgical suture needle according to a ninth aspect.

In a ninth aspect of an example RFID-enabled surgical suture needle ("suture needle") 900, as illustrated in FIG. 9, the suture needle 900 includes an RFID chip 902 positioned proximate to a swage end 918 of a metallic body 904. In this aspect, the RFID chip 902 is circumferentially wrapped around a conductive suture 906. The conductive suture 906 includes a standard suture 908 covered by a conductive coating 910. The chip-body contact 912, electrically connects one end of the wrapped RFID chip 902 to the conductive metallic swage end 918. The chip-suture contact 914, electrically connects the other end of the wrapped RFID chip 902 to the conductive suture 906. Thus, the metallic body 904 and the conductive suture 906 together form the two arms of an antenna.

Figure 10:
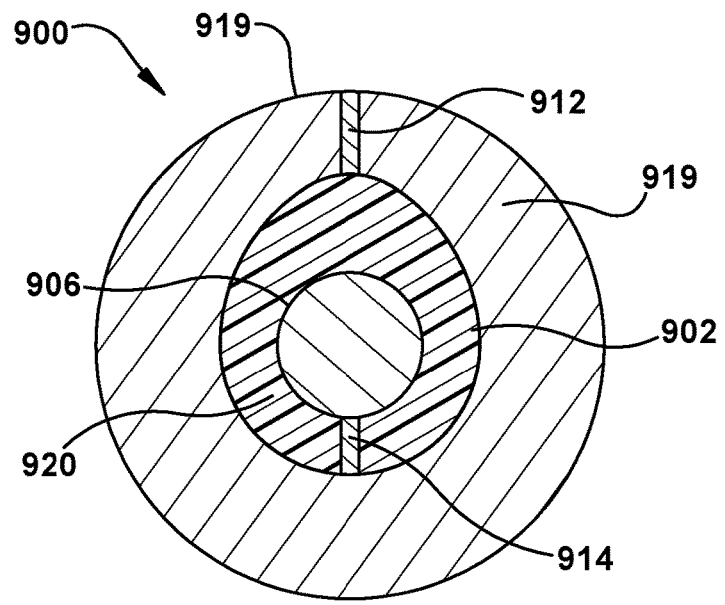
FIG. 10 is a schematic cross-sectional view of a portion of an example RFID-enabled surgical suture needle according to the ninth aspect.

As illustrated in the cross sectional view in FIG. 10, the chip-body contact 912 is supported by a circumferentially wrapped non-conductive outer layer 919. The chip-suture contact 914 is also supported by a circumferentially wrapped non-conductive inner layer 920. The inner and outer non-conductive layers 919 and 920 provide structural support to the chip-body contact 912, the chip-suture contact 914, and the RFID chip 902 and prevent inadvertent short circuiting of the chip 902.

Referring again to FIG. 9, the suture needle 900 includes an RF lucent sheath 916 constructed of RF lucent material that wraps around the conductive suture 106 and serves as an electrical insulator. The RF lucent sheath 916 is joined to the metallic body 904 at a swage end 918. In one example, a portion of the metallic body 904 may extend and partially overlap at least a portion of the RFID chip 902 and the conductive suture 906 at the swage end 918. The conductive portion of the conductive suture 906, however, is not completely overlapped by the metallic body 904, as illustrated in FIG. 9.

Figure 11:
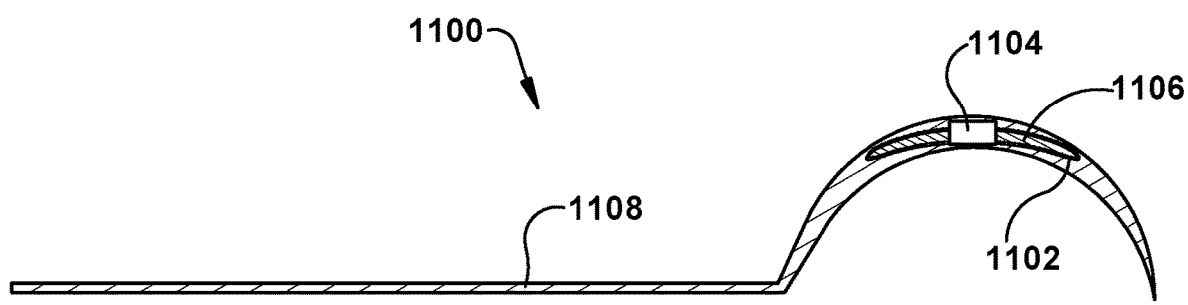
FIG. 11 is a schematic cross-sectional view of a portion of an example RFID-enabled surgical suture needle according to a tenth aspect.

In a tenth aspect of an example RFID-enabled surgical suture needle ("suture needle") 1100, as illustrated in FIG. 11, a sheath 1102 that encloses the RFID chip 1104 and antenna 1106 is made from the same RF lucent material as the suture 1108. Thus, the combination of the RFID chip 1104 and the antenna 1106 serve as the core of the suture 1108. In one example, the RF lucent material may comprise an absorbable plastic such as polyglycolic acid. In another example, the RF lucent material may comprise a non-absorbable plastic such as polypropylene. Using the same material for both the suture and the sheath enclosing the suture may eliminate a need to work with and test additional materials, thereby simplifying the manufacturing process.

Figure 12:
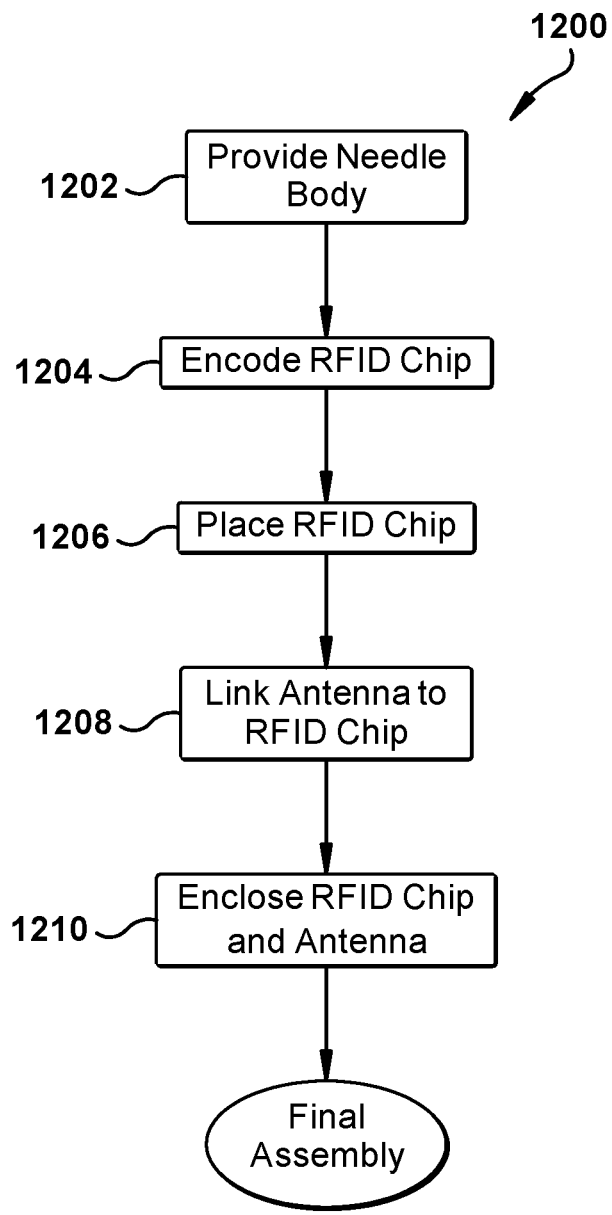
FIG. 12 is a flow chart illustrating an example method for manufacturing a suture needle apparatus.

FIG. 12 a flow chart illustrating an example method 1200 for manufacturing a suture needle apparatus. At block 1202, a needle body is provided. At block 1204, an RFID chip is encoded with information associated with the suture needle apparatus. At block 1206, the RFID chip is disposed near the needle body. In one example, the RFID chip is disposed inside a recess of the needle body and the recess is filled with epoxy or another suitable binder/potting material. At block 1208, an antenna is linked to the RFID chip. The antenna is configured to wirelessly communicate the identifying information. At block 1210, the RFID chip and the antenna are at least partially enclosed with a sheath made of RF lucent material to form a final assembly.

Figure 13:
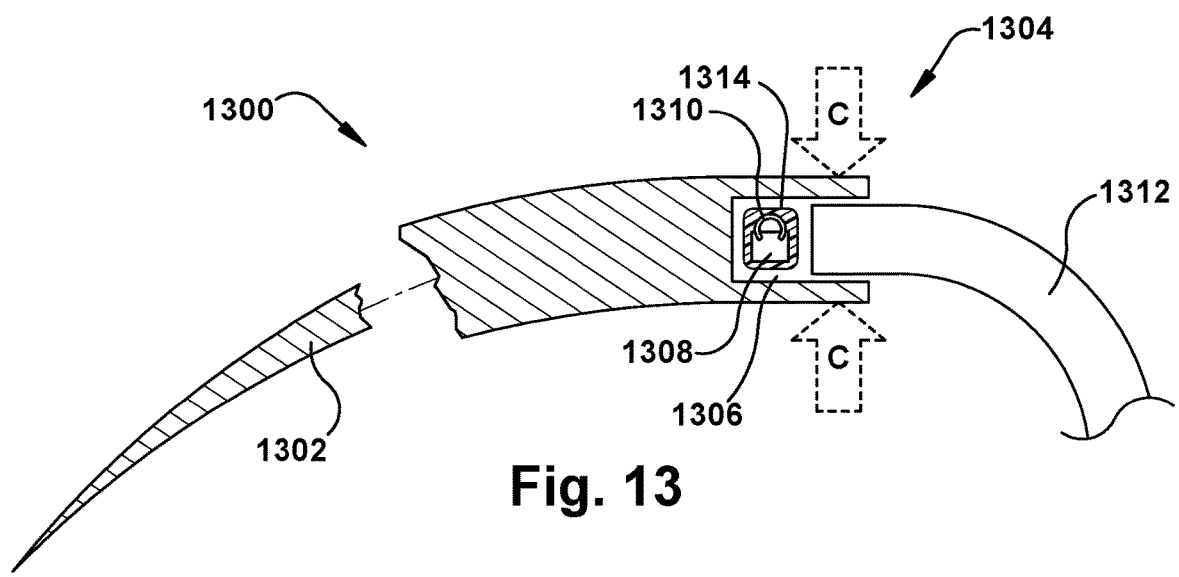
FIG. 13 is a schematic cross-sectional view of a portion of an example RFID-enabled surgical suture needle according to an eleventh aspect.

FIG. 13 illustrates an eleventh aspect of an example RFID-enabled surgical suture needle ("suture needle") 1300, which may include any of the features previously discussed with respect to other suture needles. The suture needle 1300 of FIG. 13 includes a body 1302 which is at least one of partially metallic, organic, plastic, and composite, such as by being constructed primarily of stainless steel (or other suitable material, such as, but not limited to, a steel alloy). At or near the swage end 1304, the suture needle 1300 includes a cavity or recess 1306. A radio-frequency identification ("RFID") chip 1308 disposed proximate to the needle body 1302. The RFID chip 1308 is encoded with an identifying information, which may comprise at least one of suture size, type, lot, unique identifier, and expiration date, associated with the suture needle 1300 apparatus. The RFID chip 1308 includes an electromagnetic coupling element to facilitate inductive and/or capacitive connection of the RFID chip 1308 with the needle body 1302 and/or a suture thread, such as the inductive loop 1310.

As shown in FIG. 13, the RFID chip 1308 may be at least partially disposed inside the recess 1306 of the needle body 1302. The recess 1306 may be configured to concurrently receive the RFID chip 1308 and at least a portion of a suture thread 1312 (shown here as a distal end of the suture thread 1312).

The suture thread 1312 may be of any suitable type, such as, but not limited to, silk, metallic, gut, polyglycolic acid, polylactic acid, nylon, polypropylene, polyester, or the like. The suture thread 1312 may extend from the needle body 1302, such that the suture needle 1300 may be used to draw the suture thread 1312 through a patient tissue in a known manner. The suture thread 1312 may be operatively coupled to the needle body 1302 in any desired manner. For example, the needle body may include a swaged end 1304 selectively coupled to the suture thread 1312. As shown by arrows "C" in FIG. 13, the swaged end 1304 may be crimped to directly connect the needle body 1302 and the suture thread 1312 (here, as previously mentioned, the distal end of the suture thread 1312).

Also as shown in FIG. 13, the RFID chip 1308 may be disposed axially between at least a portion of the needle body 1302 and the suture thread 1312. In the aspect shown in FIG. 13, this is accomplished by lining up the needle body 1302, the RFID chip 1308 in the recess 13016, and the suture thread 1312 longitudinally in a row as the structure is assembled.

At least one of the needle body 1302 and the suture thread 1312 may serve as an antenna selectively electromagnetically (e.g., inductively and/or capacitively) coupled to the RFID chip. When coupled, the antenna is configured to wirelessly communicate the identifying information responsive to radio-frequency interrogation of the suture needle 1300 apparatus. For example, in some use environments, at least a portion of the suture thread 1312 may comprises conductive material to provide a conductive suture thread 1312C. The conductive suture thread 1312C may be electrically isolated from the needle body 1302 (as shown and will be discussed below with respect to FIG. 14), and the conductive suture thread 1312C is at least a portion of the antenna.

Figure 15:
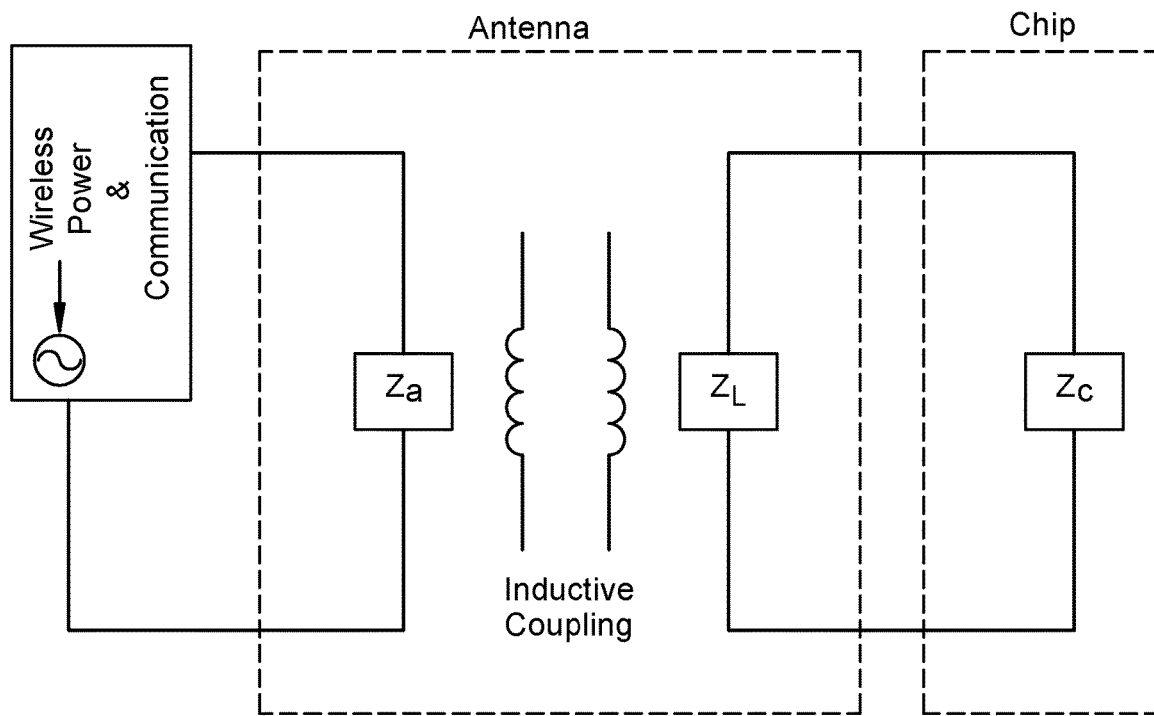
FIG. 15 is an example electric circuit diagram of at least one aspect of the RFID-enabled surgical suture needle.

With reference again to FIG. 13, the RFID chip 1308 may have a small inductive loop 1310 operatively coupled to it, when the electromagnetic coupling is done inductively. This inductive loop 1310 inductively couples to a conductive portion of the apparatus acting as an antenna, such as to a conductive portion (e.g., metal) of a conductive suture thread 1312C and/or to the needle body 1302. Therefore, the antenna (hereafter presumed to be a conductive suture thread 1312C) coupled with the inductive loop 1310 acts to collect and supply power to the RFID chip 1308 to power it up, and the RFID chip 1308 can the backscatter the identifying information back to an RFID reader, assisted by the structure acting as an antenna. This electrical relationship is shown in FIG. 15.

In order to facilitate this operation, it may be desirable, in some use environments, to electrically insulate the RFID chip 1308 (with its included inductive loop 1310) from a chosen one of the conductive suture thread 1312C and the needle body 1302 when the other one of the conductive suture thread 1312C and the needle body 1302 is acting as the antenna. To that end, and using a conductive suture thread 1312C as an example antenna, the RFID chip 1308 may be at least partially enclosed within a nonconductive shell 1314, as shown in FIG. 13. The nonconductive shell 1314, when present, is configured to electrically isolate the RFID chip 1308 from the needle body 1302. The nonconductive shell 1314 should, in most use environments, entirely three-dimensionally surround the RFID chip 1308 and can be made of any material, including, but not limited to, polymers, silicone, hot glue, parylene, glass, ceramic, plastic, paper or cellulose-based materials, and/or any other similarly nonconductive materials. Similarly, the RFID chip 1308 can be enclosed within the nonconductive shell 1314 in any desired manner including, but not limited to, placement and curing of a flowable hardening material around the RFID chip 1308 and assembly of a preconfigured nonconductive shell 1314 around the RFID chip 1308 (e.g., a multipiece shell or a shell having an opening to selectively admit the RFID chip 1308 therethrough).

Figure 14:
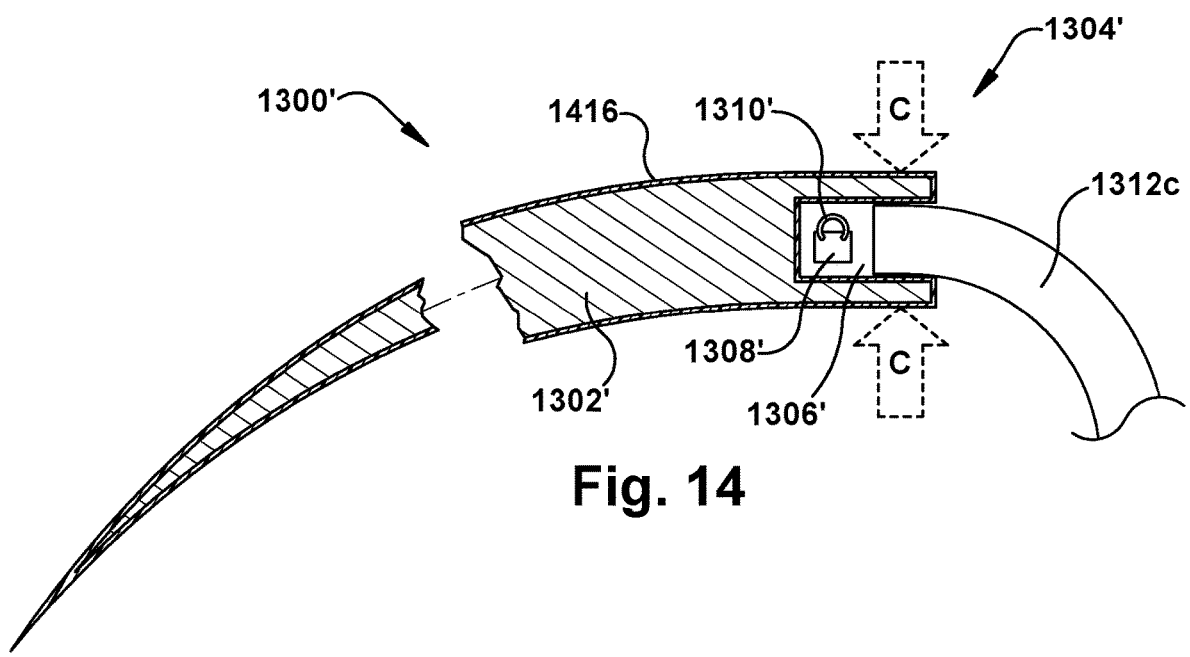
FIG. 14 is a schematic cross-sectional view of a portion of an example RFID-enabled surgical suture needle according to a twelfth aspect.

FIG. 14 illustrates a twelfth aspect of a suture needle. The suture needle of FIG. 14 is similar to the suture needle of FIG. 13 and therefore, structures of FIG. 14 that are the same as or similar to those described with reference to FIG. 13 have the same reference numbers with the addition of a "prime" mark. Description of common elements and operation similar to those in the previously described eleventh aspect, or any other aspect herein, will not be repeated with respect to the twelfth aspect, but should instead be considered to be incorporated below by reference as appropriate.

In the suture needle 1300' of FIG. 14, the needle body 1302' is at least partially coated with a nonconductive skin 1416 configured to electrically isolate the RFID chip 1308' from the needle body 1302'. This nonconductive skin 1416 may cover all of the needle body 1302' or just a portion (e.g., an interior of the recess 1306') which is likely to come into unwanted otherwise-conductive contact with the RFID chip 1308' and/or its included inductive loop 1310'. The nonconductive skin 1416 may be homogenously applied to the needle body 1302' in any desired manner, including a hardening liquid coating (e.g., parylene) and/or a shrink-wrapped sheath, and may be made of any suitable material or combination of materials. It is contemplated that the nonconductive skin 1416 may have different thicknesses at different areas of the needle body 1302'.

Figure 16:
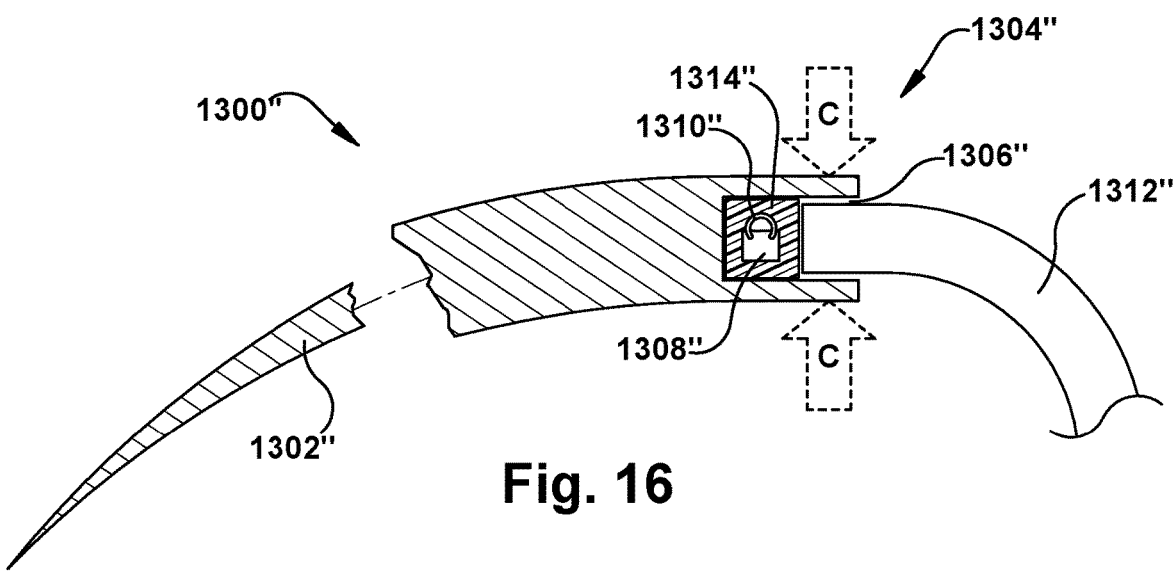
FIG. 16 is a schematic cross-sectional view of a portion of an example RFID-enabled surgical suture needle according to a thirteenth aspect.
Figure 22A:
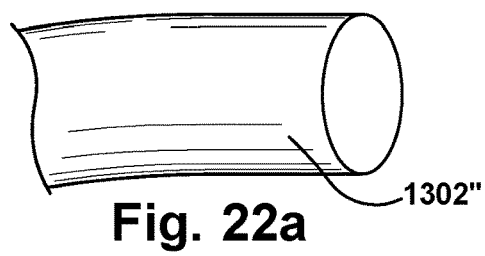
FIGS. 22*a-f* schematically depict an example assembly sequence of the RFID-enabled surgical suture needle of FIG. 16.
Figure 22B:
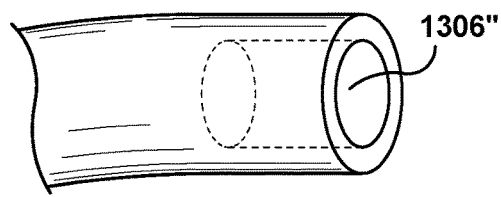

FIG. 16 illustrates a thirteenth aspect of a suture needle. The suture needle of FIG. 16 is similar to the suture needle of FIG. 13 and therefore, structures of FIG. 16 that are the same as or similar to those described with reference to FIG. 13 have the same reference numbers with the addition of a double "prime" mark. Description of common elements and operation similar to those in the previously described eleventh aspect, or any other aspect herein, will not be repeated with respect to the thirteenth aspect, but should instead be considered to be incorporated below by reference as appropriate.

Suture needle 1300" shown in FIG. 16 is somewhat similar to that of FIG. 13, in that the needle body 1302" includes a recess 1306" for selectively receiving the RFID chip 1308", and the RFID chip 1308" and inductive loop 1310" are enclosed within a nonconductive shell 1314". However, in FIG. 16, the nonconductive shell 1314" closely conforms to at least one inner dimension of the recess 1306". Indeed, the nonconductive shell 1314" may be selectively frictionally engaged (i.e., press-fit) into the recess 1306", potted into the recess 1306", or otherwise placed into the configuration depicted in FIG. 16.

With this "plug-type" nonconductive shell 1314", the distal end of the suture thread 1312" can be butted up against, or even inserted slightly into, a proximal surface of the nonconductive shell 1314" before crimping. As opposed to the suture needle 1300 of FIG. 13, the suture needle 1300" of FIG. 16 may allow a fabricator to have greater control over the orientation and positioning of the RFID chip 1308" within the recess 1306", which may assist with standardization, quality control, and even operability of the suture needle 1300" apparatus.

FIGS. 17-18 illustrate a fourteenth aspect of a suture needle. The suture needle of FIGS. 17-18 is similar to the suture needle of FIG. 13 and therefore, structures of FIGS. 17-18 that are the same as or similar to those described with reference to FIG. 13 have the same reference numbers with the addition of a triple "prime" mark. Description of common elements and operation similar to those in the previously described eleventh aspect, or any other aspect herein, will not be repeated with respect to the fourteenth aspect, but should instead be considered to be incorporated below by reference as appropriate.

FIG. 18 is an exploded view of the suture needle 1300''' apparatus of FIG. 17. This fourteenth aspect differs from those previously described at least because the RFID chip 1308''' has an annular profile, including a center aperture 1718 configured to selectively receive at least a portion of the suture thread 1312'''. The needle body 1302''' includes a recess 1306''' for selectively concurrently receiving the annular RFID chip 1308''' and a portion of the suture thread 1312'''. There may be at least one washer 1720 which mechanically and/or electrically isolates the annular RFID chip 1308''' from other structures of the apparatus. For example, and as shown in FIG. 17, the washer 1720 (which may be an insulating washer) may be longitudinally interposed between a rim 1722 of the recess 1306''' and the annular RFID chip 1308''', with the suture thread 1312''' extending entirely axially through both the washer 1720 and the RFID chip 1308''' and the distal end of the suture thread 1312''' being crimped into the recess 1306'''. In this case, the RFID chip 1308''' is not located, or not entirely located, in the recess 1306''' but is still proximate the needle body 1302'''.

In the aspect of FIGS. 17-18, the suture needle 1300''' apparatus may include a hollow cap 1724 fitting about a circumference of the suture thread 1300" for preventing egress of the RFID chip 1308''' from the suture needle 1300'''. Accordingly, the combination of the washer 1720 and cap 1724 may serve to electrically insulate the annular RFID chip 1308''' from the needle body 1302''' while holding the RFID chip 1308''' in inductively and/or directly conductive contact (or any other electromagnetic contact) with the suture thread 1300'''. Use of the cap 1724 may help to smooth a mechanical transition between the needle body 1302''' and suture thread 1300''', and therefore assist in avoiding "catching" of the suture needle 1300''' apparatus and/or provide a lower-profile transition area than if the RFID chip 1308''' were to be located inside a recess 1306''' of the needle body 1302'''.

A method of providing any of the suture needle apparatuses of at least FIGS. 13-18 may include providing a needle body 1300 and providing an RFID chip 1308 including an inductive loop 1310. (The numbering of FIG. 13 only is used here and below for simplicity, but does not preclude this description applying also or instead to the aspects of FIGS. 14-18. Also, the electromagnetic coupling is referenced herein as inductive coupling, for ease of description.) The RFID chip 1308 is encoded with information associated with the suture needle 1300 apparatus. The RFID chip 1308 is disposed proximate to the needle body 1302, which can include includes disposing at least a portion of the RFID chip 1308 inside a recess 1306 of the needle body 1302.

A suture thread 1312 is operatively coupled to the needle body 1302, such as by swaging the suture needle 1300 with the suture thread 1312. At least one of the needle body 1302 and the suture thread 1312 is inductively coupled to the RFID chip 1308 to serve as an antenna. When the suture thread 1312 is serving as the antenna, the RFID chip 1308 may be electrically isolated from the needle body 1302. For example, this isolation may be accomplished by at least partially enclosing the RFID chip 1308 within a nonconductive shell 1314—which could include closely conforming the nonconductive shell 1314 to at least one inner dimension of the recess 1306—and/or at least partially coating the needle body 1302 with a nonconductive skin 1416.

It is contemplated that the RFID chip 1308 could also or instead be provided with an annular profile including a center aperture 1718. In this case, at least a portion of the suture thread 1312 is extended through the center aperture 1718. Concurrently with the RFID chip 1308 surrounding at least a portion of the suture thread 1312, an other portion of the suture thread 1312 is placed into a recess 1306 of the needle body 1302. With a cap 1724 fit about a circumference of the suture thread 1312, egress of the RFID chip 1308 from the suture needle 1300 is provided. This is another way that the RFID chip 1308 can be electrically isolated from the needle body.

Regardless of how the electrical isolation occurs, though, when the antenna and the RFID chip 1308 are inductively coupled, the identifying information can be wirelessly communicated as desired responsive to radio-frequency interrogation of the suture needle 1300 apparatus.

FIGS. 19a-23h schematically depict assembly of, respectively, a prior art (non-RFID-equipped) suture needle (numbered analogously to FIG. 13), the RFID-enabled surgical suture needle of FIG. 13, the RFID-enabled surgical suture needle of FIG. 14, the RFID-enabled surgical suture needle of FIG. 16, and the RFID-enabled surgical suture needle of FIGS. 17-18. The various views of FIGS. 19a-23h can happen concurrently and/or sequentially, and in any order including an order different than the lower-case lettering would seem to indicate.

In each of FIGS. 19a-23h, a needle body 1302 is provided in view (a), and a recess 1306 is generated in a proximal end of the needle body 1302 in view (b).

With specific reference to the prior art (non-RFID-equipped) suture needle 1300 of FIGS. 19a-d, a suture thread 1312 is inserted into the recess 1306 in view (c) and the suture thread 1312 is crimped (represented by arrows "C") in view (d). The prior art suture needle 1300 is then complete.

FIGS. 20a-22f schematically depict assembly of the RFID-enabled surgical suture needles of FIGS. 13, 14, and 15, respectively. In each of FIGS. 20a-22f, view (d) depicts the insertion of the RFID chip 1308 and inductive loop 1310 into the recess 1306, a suture thread 1312 is inserted into the recess 1306 in view (e) and the suture thread 1312 is crimped (represented by arrows "C") in view (f) to complete the suture needle 1300 apparatus. The assembly differences in FIGS. 20a-22f occur in view (c).

Figure 21A:
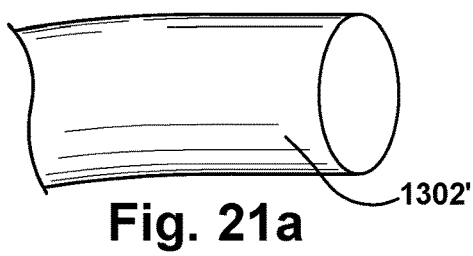
FIGS. 21*a-f* schematically depict an example assembly sequence of the RFID-enabled surgical suture needle of FIG. 14.
Figure 21B:
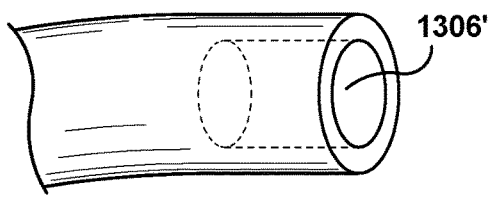
Figure 21C:
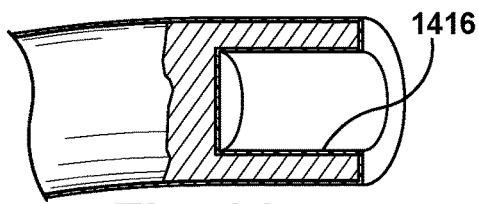
Figure 22C:
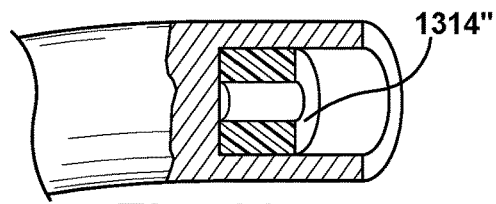
Figure 21D:
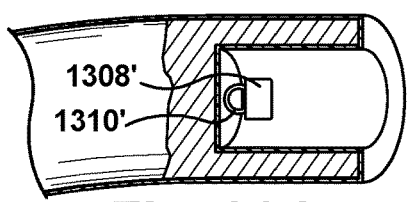
Figure 22D:
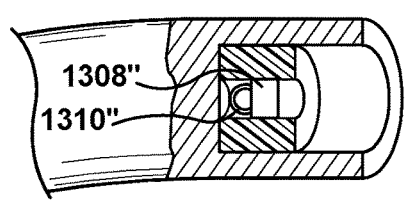
Figure 21E:
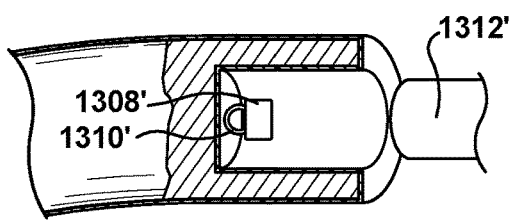
Figure 22E:
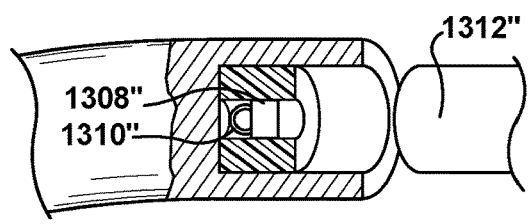
Figure 21F:
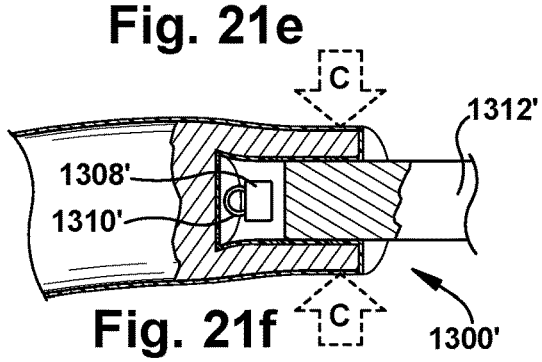
Figure 22F:
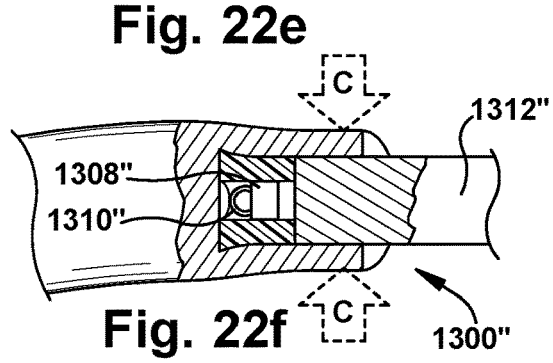

In FIG. 20c, the nonconductive shell 1314 is provided to the recess 1306 to receive the RFID chip 1308 and the inductive loop 1310. In FIG. 21c, the nonconductive skin 1416 is provided to at least the recess 1306' and optionally to the entire needle body 1302'. In FIG. 22c, the plug-type nonconductive shell 1314" is provided to the recess 1306 to receive the RFID chip 1308 and the inductive loop 1310.

Figure 23A:
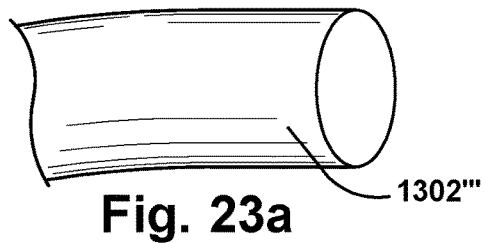
FIGS. 23*a-h* schematically depict an example assembly sequence of the RFID-enabled surgical suture needle of FIG. 17.
Figure 23E:
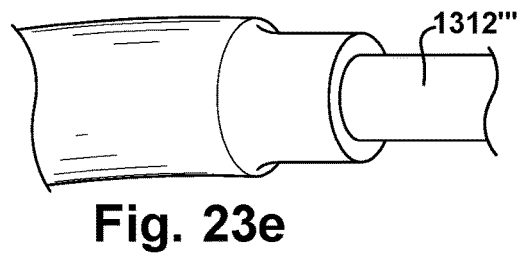
Figure 23B:
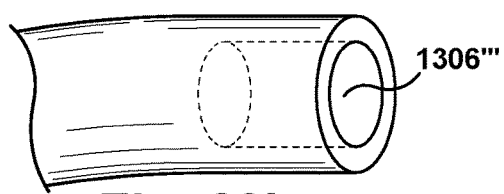
Figure 23F:
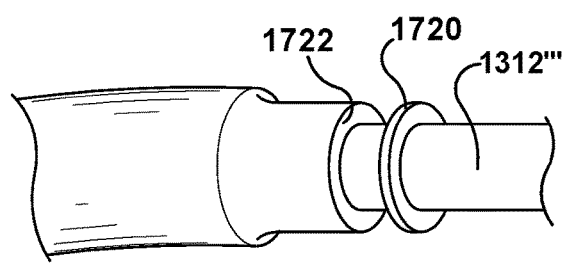
Figure 23C:
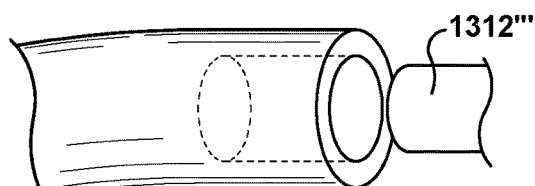
Figure 23G:
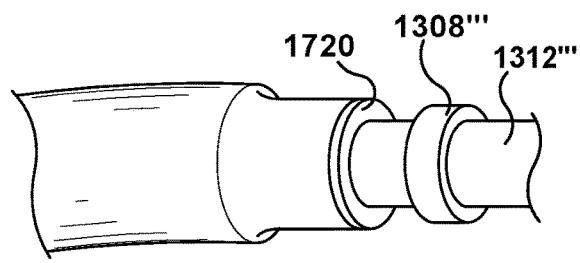
Figure 23D:
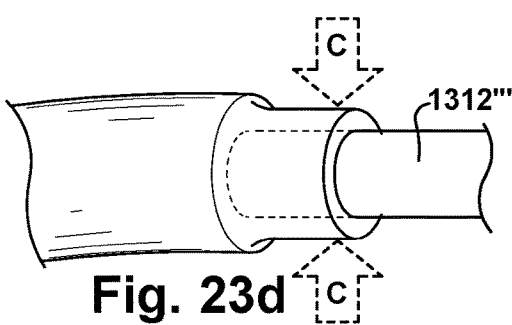
Figure 23H:
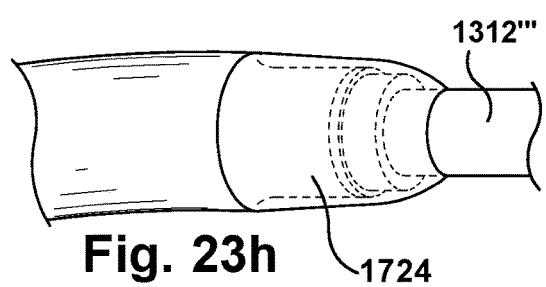

In FIGS. 23a-h, a needle body 1302 is provided in view (a), and a recess 1306 is generated in a proximal end of the needle body 1302 in view (b). However, due to the aforementioned differences between the aspects of FIGS. 13-16 and FIGS. 17-18, FIG. 23c depicts the suture thread 1312''' being inserted into the recess 1306''', and crimped into place (arrows "C") in views (d)-(e). Then, in FIG. 23f, a washer 1720 is slid down over the suture thread 1312''' and optionally into contact with a rim 1722 of the recess 1306'''. FIG. 23g shows the annular RFID chip 1308''' (and any associated inductive loops 1310''') being slid down over the suture thread 1312''' and into contact with any washer 1720 that was provided. Finally, in FIG. 2h3, the cap 1724 is installed to cover the washer 1720 (when present) and annular RFID chip 1308''' to complete the assembly.

It is contemplated that the antenna, whether associated with the needle body 1302 or the conductive suture thread 1312 will be electrically isolated from the inductive loop on the RFID chip 1308, for most use environments. Complete electrical isolation between the needle 1300 and conductive thread 1312 may be desired in some use environments, as well, but may be optional in others.

While the RFID chip 1308 is disclosed as being disposed axially between the needle body 1302 and the suture thread 1312 (i.e., at the swage end of the needle), it is contemplated that any RFID chip(s), of any examples or aspects of the technology described herein, could be located as desired anywhere in/on the needle and/or thread including, but not limited to, at the mid-section or pointed tip of the needle.

Various aspects of the present technology are described below, in claim-mimicking format:

Aspect 1. A suture needle apparatus comprising: a needle body;
a radio-frequency identification ("RFID") chip disposed proximate to the needle body, the RFID chip encoded with an identifying information associated with the suture needle apparatus;
an antenna spanning at least a portion of the needle body and configured to wirelessly communicate the identifying information; and
a sheath comprising radio frequency ("RF") lucent material coextensive with and at least partially enclosing the RFID chip and the antenna.

Aspect 2. The suture needle apparatus of aspect 1, wherein the sheath encloses at least a portion of the needle body.

Aspect 3. The suture needle apparatus of aspect 1, wherein the antenna comprises at least a portion of the needle body.

Aspect 4. The suture needle apparatus of aspect 1, wherein the RFID chip is disposed inside the needle body.

Aspect 5. The suture needle apparatus of aspect 1, wherein the RFID chip is potted inside a recess of the needle body.

Aspect 6. The suture needle apparatus of aspect 1, wherein the needle body is at least one of partially metallic, organic, plastic, and composite.

Aspect 7. The suture needle apparatus of aspect 1, wherein the antenna at least partially envelops the body and RFID chip.

Aspect 8. The suture needle apparatus of aspect 1, further comprising a suture extending from the needle body.

Aspect 9. The suture needle apparatus of aspect 8, further comprising an eye loop for receiving the suture.

Aspect 10. The suture needle apparatus of aspect 8, further comprising a swaged end coupled to the suture.

Aspect 11. The suture needle apparatus of aspect 8, wherein at least a portion of the suture comprises conductive material to provide a conductive suture, wherein the conductive suture is electrically isolated from the needle body, and wherein the conductive suture and needle body are connected to opposite terminals of a chip, thereby forming separate arms of the antenna.

Aspect 12. The suture needle apparatus of aspect 8, wherein the RFID chip spans the needle body and the suture.

Aspect 13. The suture needle apparatus of aspect 12, wherein the RFID chip is disposed axially between the needle body and the suture.

Aspect 14. The suture needle apparatus of aspect 13, wherein the RFID chip is wrapped around the suture.

Aspect 15. The suture needle apparatus of aspect 14, including: an outer layer wrapped around the RFID chip between the RFID chip and the needle body to connect the needle body to the RFID chip; and
an inner layer wrapped around the suture between the suture and the RFID chip to connect the suture to the RFID chip.

Aspect 16. The needle apparatus of aspect 1, wherein identifying information comprises at least one of suture size, type, lot, unique identifier, and expiration date.

Aspect 17. A suture needle apparatus comprising: a metallic needle body;
a suture extending from the metallic body, wherein the suture comprises conductive material,
a radio-frequency identification ("RFID") chip disposed axially between the body and the suture, the RFID chip encoded with an identifying information associated with the suture needle apparatus;
an antenna, comprising at least a portion of the metallic body, linked to the RFID chip, the antenna configured to wirelessly communicate the identifying information; and
a protective sheath comprising RF lucent material, enclosing the RFID chip and antenna;
wherein the conductive suture is electrically isolated from the sheath, and wherein the conductive suture is coupled to the antenna, thereby forming an extension of the antenna.

Aspect 18. The suture needle apparatus of aspect 17, including:

an outer layer disposed between the RFID chip and the needle body to connect the needle body to the RFID chip; and
an inner layer disposed between the suture and the RFID chip to connect the suture to the RFID chip.

Aspect 19. The suture needle of aspect 17, wherein the suture is electrically isolated from the protective sheath, and wherein the conductive suture is coupled to the antenna, thereby forming an extension of the antenna.

Aspect 20. A method for manufacturing a suture needle apparatus, the method comprising: providing a needle body; encoding a radio-frequency identification ("RFID") chip with information associated with the suture needle apparatus;
disposing the RFID chip proximate to the needle body; linking an antenna to the RFID chip, the antenna configured to wirelessly communicate the identifying information; and at least partially enclosing the RFID chip and the antenna with a sheath comprising RF lucent material.

Aspect 21. The method of aspect 20, wherein disposing the RFID chip proximate to the needle body includes disposing the RFID chip inside a recess of the needle body.

Aspect 22. The method of aspect 20, including swaging the suture needle with a suture.

Aspect 23. The method of aspect 22, including at least partially coating the suture with a conductive material.

Aspect 24. The method of aspect 23, including circumferentially wrapping the RFID chip around the suture.

Unless defined otherwise, all technical and scientific terms used herein have the same meaning as is commonly understood by one of skill in the art to which the present disclosure pertains.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

As used herein, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the phrase "at least one of X and Y" can be interpreted to include X, Y, or a combination of X and Y. For example, if an element is described as having at least one of X and Y, the element may, at a particular time, include X, Y, or a combination of X and Y, the selection of which could vary from time to time. In contrast, the phrase "at least one of X" can be interpreted to include one or more Xs. It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "directly adjacent" another feature may have portions that overlap or underlie the adjacent feature, whereas a structure or feature that is disposed "adjacent" another feature might not have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of a device in use or operation, in addition to the orientation depicted in the figures. For example, if a device in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. In an effort to maintain clarity in the Figures, certain ones of duplicative components shown have not been specifically numbered, but one of ordinary skill in the art will realize, based upon the components that were numbered, the element numbers which should be associated with the unnumbered components; no differentiation between similar components is intended or implied solely by the presence or absence of an element number in the Figures. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications. Any of the described structures and components could be disposable or reusable as desired for a particular use environment. Any component could be provided with a user-perceptible marking to indicate a material, configuration, at least one dimension, or the like pertaining to that component, the user-perceptible marking potentially aiding a user in selecting one component from an array of similar components for a particular use environment. A "predetermined" status may be determined at any time before the structures being manipulated actually reach that status, the "predetermination" being made as late as immediately before the structure achieves the predetermined status. The term "substantially" is used herein to indicate a quality that is largely, but not necessarily wholly, that which is specified—a "substantial" quality admits of the potential for some relatively minor inclusion of a non-quality item. Though certain components described herein are shown as having specific geometric shapes, all structures of this disclosure may have any suitable shapes, sizes, configurations, relative relationships, cross-sectional areas, or any other physical characteristics as desirable for a particular application. It should be understood that elements shown as a single component may be replaced with multiple components, and elements shown as multiple components may be replaced with a single component. The drawings are not to scale and the proportion of certain elements may be exaggerated for the purpose of illustration. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages can be obtained from a study of the drawings, the disclosure, and the appended claims.

We claim:

1. A suture needle apparatus comprising:
   a needle body;
   a radio-frequency identification ("RFID") chip disposed proximate to the needle body, the RFID chip encoded with an identifying information associated with the suture needle apparatus, and the RFID chip including an electromagnetic coupling element; and
   a suture thread operatively coupled to the needle body;
   wherein the RFID chip is disposed axially between the needle body and the suture thread;
   wherein the RFID chip and at least a portion of a suture thread are concurrently received within a recess of the needle body, the RFID chip being longitudinally interposed between the suture thread and at least a portion of the needle body; and
   wherein at least one of the needle body and the suture thread is an antenna selectively electromagnetically coupled to the RFID chip and, when coupled, is configured to wirelessly communicate the identifying information responsive to radio-frequency interrogation of the suture needle apparatus.

2. The suture needle apparatus of claim 1, wherein the RFID chip is at least partially disposed inside a recess of the needle body.

3. The suture needle apparatus of claim 2, wherein the needle body includes a recess configured to concurrently receive the RFID chip and at least a portion of the suture thread.

4. The suture needle apparatus of claim 1, wherein the needle body is at least one of partially metallic, organic, plastic, and composite.

5. The suture needle apparatus of claim 1, wherein the suture thread extends from the needle body.

6. The suture needle apparatus of claim 5, wherein the needle body includes a swaged end coupled to the suture thread.

7. The suture needle apparatus of claim 6, wherein the swaged end is crimped to directly connect the needle body and the suture thread.

8. The suture needle apparatus of claim 1, wherein at least a portion of the suture comprises conductive material to provide a conductive suture thread, wherein the conductive suture thread is electrically isolated from the needle body, and wherein the conductive suture thread is at least a portion of the antenna.

9. The needle apparatus of claim 1, wherein identifying information comprises at least one of suture size, type, lot, unique identifier, and expiration date.

10. The suture needle apparatus of claim 1, wherein the RFID chip is at least partially enclosed within a nonconductive shell configured to electrically isolate the RFID chip from the needle body.

11. The suture needle apparatus of claim 10, wherein the needle body includes a recess for selectively receiving the RFID chip, and wherein the nonconductive shell closely conforms to at least one inner dimension of the recess.

12. The suture needle apparatus of claim 11, wherein the nonconductive shell is selectively frictionally engaged into the recess.

13. The suture needle apparatus of claim 1, wherein the needle body is at least partially coated with a nonconductive skin configured to electrically isolate the RFID chip from the needle body.

14. The suture needle apparatus of claim 1, wherein the RFID chip has an annular profile including a center aperture configured to selectively receive at least a portion of the suture thread.

15. The suture needle apparatus of claim 14, wherein the needle body includes a recess for selectively concurrently receiving the RFID chip and a portion of the suture thread, the needle apparatus including a cap fitting about a circumference of the suture thread for preventing egress of the RFID chip from the suture needle.

16. The suture needle apparatus of claim 1, wherein the electromagnetic coupling is inductive coupling.

17. A method of providing a suture needle apparatus, the method comprising:
   providing a needle body;
   providing a radio-frequency identification ("RFID") chip including an electromagnetic coupling element;
   encoding the RFID chip with information associated with the suture needle apparatus;
   disposing the RFID chip proximate to the needle body;
   operatively coupling a suture thread to the needle body with the RFID chip disposed axially between the needle body and the suture thread, including concurrently receiving the RFID chip and at least a portion of a suture thread within a recess of the needle body, the RFID chip being longitudinally interposed between the suture thread and at least a portion of the needle body;
   selectively electromagnetically coupling at least one of the needle body and the suture thread to the RFID chip as an antenna; and
   when the antenna and the RFID chip are electromagnetically coupled, wirelessly communicating the identifying information responsive to radio-frequency interrogation of the suture needle apparatus.

18. The method of claim 17, including electrically isolating the RFID chip from the needle body.

19. The method of claim 18, including
providing the RFID chip with an annular profile including a center aperture;
extending at least a portion of the suture thread through the center aperture;
concurrently with the RFID chip surrounding at least a portion of the suture thread, placing an other portion of the suture thread into a recess of the needle body; and
with a cap fit about a circumference of the suture thread, preventing egress of the RFID chip from the suture needle.

* * * * *